(12) United States Patent
Ross et al.

(10) Patent No.: US 7,655,755 B2
(45) Date of Patent: *Feb. 2, 2010

(54) BREAST CANCER RESISTANCE PROTEIN (BCRP) AND THE DNA WHICH ENCODES IT

(75) Inventors: Douglas D. Ross, Columbia, MD (US); L. Austin Doyle, Silver Spring, MD (US); Lynne V. Abruzzo, Potomac, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 515 days.

This patent is subject to a terminal disclaimer.

(21) Appl. No.: 11/184,860

(22) Filed: Jul. 20, 2005

(65) Prior Publication Data

US 2005/0272684 A1 Dec. 8, 2005

Related U.S. Application Data

(62) Division of application No. 09/961,086, filed on Sep. 21, 2001, now Pat. No. 7,541,437, which is a division of application No. 09/245,808, filed on Feb. 5, 1999, now Pat. No. 6,313,277.

(60) Provisional application No. 60/073,763, filed on Feb. 5, 1998.

(51) Int. Cl.
*C07K 14/00* (2006.01)

(52) U.S. Cl. ...................................... 530/350
(58) Field of Classification Search .................. 530/350
See application file for complete search history.

(56) References Cited

U.S. PATENT DOCUMENTS

| 5,585,479 | A | 12/1996 | Hoke | |
|---|---|---|---|---|
| 6,060,248 | A | 5/2000 | Lane | |
| 2003/0232362 | A1* | 12/2003 | Komatani et al. | 435/6 |

FOREIGN PATENT DOCUMENTS

| WO | 94/10303 | 5/1994 |
|---|---|---|
| WO | 98/55614 | 12/1998 |
| WO | 99/58675 | 11/1999 |
| WO | 00/18912 | 4/2000 |
| WO | 00/36101 | 6/2000 |

OTHER PUBLICATIONS

Doyle et al (PNAS, 1999, 96:2569).*
Lazar et al (Molecular and Cellular Biology, 1988, 8:1247-1252).*
Freshney (Culture of Animal Cells, A Manual of Basic Technique, Alan R. Liss, Inc., 1983, New York, p. 4).*
Dermer (Bio/Technology, 1994, 12:320).*
Zips et al (In vivo, 2005, 19:1-7).*
Brennan et al (Journal of Autoimmunity, 1989, vol. 2 suppl., pp. 177-186).*
Zimmer (Cell Motility and the Cytoskeleton, 1991, vol. 20, pp. 325-337).*
Eriksson et al (Diabetologia, 1992, vol. 35, pp. 143-147).*
Hell et al (Laboratory Investigation, 1995, vol. 73, pp. 492-496).*
Powell et al (Pharmacogenesis, 1998, vol. 8, pp. 411-421).*
Carrere et al (Gut, 1999, vol. 44, pp. 545-551).*
Vallejo et al (Biochimie, 2000, vol. 82, pp. 1129-1133).*
Guo et al (Journal of Pharmacology and Experimental Therapeutics, 2002, vol. 300, pp. 206-212).*
Jang et al (Clinical and Experimental Metastasis, 1997, vol. 15, pp. 469-483).*
Greenbaum et al. (Genome Biology, 2003, vol. 4, Issue 9, pp. 117.1-117.8).*
(Jansen, et al, 1995, Pediatric Res., 37(6):681-686).*
Alberts et al. (Molecular Biology of the Cell, 3rd edition, 1994, p. 465).*
Shantz and Pegg (Int J of Biochem and Cell Biol., 1999, vol. 31, pp. 107-122).*
McClean and Hill (Eur J of Cancer, 1993, vol. 29A, pp. 2243-2247).*
Fu et al (EMBO Journal, 1996, vol. 15, pp. 4392-4401).*
O'Hare et al (J Mol Bio, Dec. 1984, 3:abstract).*
Turid Knutsen et al., "Amplification of 4q21-q22 and the MXR Gene in Independently Derived Mitoxantrone-Resistant Cell Lines," *Genes, Chromosomes and Cancer*, vol. 27, pp. 110-116.
Douglas D. Ross et al., "Atypical Multidrug Resistance: Breast Cancer Resistance Protein Messenger RNA Expression in Mitaxantrone-Selected Cell Lines," *JNCI*, Jan. 28, 1999, pp. 1-11, vol. 91, No. 5.
Rando Allikmets et al., "Characterization of the Human ABC Superfamily: Isolation and Mapping of 21 New Genes Using the Expressed Sequence Tags Database," *Human Molecular Genetics*, 1996, pp. 1649-1655, vol. 5, No. 1.
S.P.C. Cole et al., "Overexpression of a Transporter Gene in a Multidrug-Resistant Human Lung Cancer Cell Line," Dec. 4, 1992, pp. 1650-1654, vol. 258.
Masayuki Nakagawa et al., "Reduced Intracellular Drug Accumulation in the Absence of P-Glycoprotein (mdr1) Overexpression in Mitoxantrone-Resistant Human MCF-7 Breast Cancer Cells," *Cancer Research*, Nov. 15, 1992, pp. 6175-6181, vol. 51.
Chih-Hsin J. Yang et al., "Cross-Resistance to Campotothecin Analogues in a Mitoxantrone-Resistant Human Breast Carcinoma Cell Line Is Not Due to DNA Topoisomerase I Alterations," *Cancer Research*, Sep. 15, 1995, pp. 4004-4009, vol. 55.
Yi-Nan Chen et al., "Characterization of Adriamycin-Resistant Human Breast Cancer Cells Which Display Overexpression of a Novel Resistance-Related Membrane Protein," *The Journal of Biological Chemistry*, Jun. 15, 1999, pp. 10073-10080, vol. 265, No. 17.
Manfred Dietel et al., "Membrane Vesicle Formation Due Acluired Mitoxantrone Resistance in Human Gastric Carcinoma Cell Line EPG85-257," *Cancer Research*, Sep. 15, 1990, pp. 6100-6106, vol. 50.
C. W. Taylor et al., "Different Mechanisms of Decreased Drug Accumulation in Doxorubicin and Mitoxantrone Resistant Variants of the MCF7 Human Breast Cancer Cell Line," 1991, pp. 923-929, vol. 63.
Sridhar K. Radindran et al., "Fumitremorigin C Reverse Multidrug Resistance in Cells Transfected with the Breast Cancer Resistance Protein," *Cancer Research*, Jan. 1, 2000, pp. 47-50, vol. 60.
Bernard W. Futscher et al., "Analysis of MRP mRNA in Mitoxantrone-Selected, Multidrug-Resistant Human Tumor Cells," *Biochemical Pharmacology*, 1994, pp. 1601-1606, vol. 47.

(Continued)

*Primary Examiner*—Sean E Aeder

(57) ABSTRACT

The Breast Cancer Resistance Protein is described, as well as the cDNA encoding said protein. This protein has been found to confer resistance to cancer chemotherapeutic drugs.

4 Claims, 25 Drawing Sheets

OTHER PUBLICATIONS

William S. Dalton et al., "Cytogenetic and Penotypic Analysis of a Human Colon Carcinoma Cell Line Resistant to Mitoxantrone," *Cancer Research*, Apr. 1, 1988, pp. 1882-1888, vol. 48.

Jong Seok Lee et al., "Reduced Drug Accumulation and Multidrug Resistance in Human Breast Cancer Cells without Associated P-Glycoprotein or MPR Overexpression," *Journal of Cellular Biochemistry*, 1997, pp. 513-526, vol. 65.

Udo Kellner et al., "Decreased Drug Accumulation in a Mitoxantrone-Resistant Gastric Carcinoma Cell Line in the Absence of P-Glycoprotein," *Int. J. Cancer*, 1997, pp. 817-824, vol. 71.

J. Ma et al., "Reduced Cellular Accumulation of Topotecan: A Novel Mechanism of Resistance in a Human Ovarian Cancer Cell Line," *British Journal of Cancer*, 1998, pp. 1645-1652, vol. 77(10).

Sridhar K. Rabindran et al., "Reversal of a Novel Multidrug Resistance Mechanism in Human Colon Carcinoma Cells by Fumitremorgin C," *Cancer Research*, Dec. 15, 1998, pp. 5850-5858, vol. 58.

Marc Maliepaards et al., "Overexpression of the BCRP/MXR/ABCP Gene in a Toptecan-Selected Ovarian Tumor Cell Line," *Cancer Research*, Sep. 15, 1999, pp. 4559-4563, vol. 59.

H Lage et al., "Expression of the Novel Mitoxantrone Resistance Associated Gene MXR7 in Colorectal Malignancies," *Intnl. Journal of Clinical Pharmacology and Therapeutics*, 1998, pp. 58-60, vol. 36, No. 1.

John D. Allen et al., "The Mouse bcrp1/Mxr/Abcp Gene: Amplification and Overexpession in Cell Lines Selected Resistance Toptecan, Mitoxantrone or Doxorubicin," *Cancer Research*, Sep. 1, 1999, pp. 4237-4424.

Lori A. Hazlehurst et al., "Multiple Mechanisms Confer Drug Resistance to Mitoxantrone in the Human 8226 Myeloma Cell Line," *Cancer Research*, Mar. 1, 2000, pp. 1-8, vol. 59.

Erasmus Schneider et al., "Multidrug Resistance-Associated Protein Gene Overexpression and Reduced Drug Sensitivity of Topoisomerase II in a Human Breast Carcinoma MCF7 Cell Line Selected for Etoposide Resistance," *Cancer Research*, Jan. 1, 1994, pp. 152-158, vol. 54.

Craig R. Fairchild et al., "Isolated of Amplified and Overexpressed DNA Sequences from Adriamycin-Resistant Human Breast Cancer Cells," *Cancer Research*, Oct. 1, 1987, pp. 5141-5148, vol. 47.

P.S. Holm et al., Reversion of Multidrug Resistance in the P-glycoprotein-positive Human Pancreatic Cell Line 1 (EPP85-181RDB) by Introduction of a Hammerhead Ribzyme.

D.D. Ross, "Novel Mechanisms of Drug Resistance in Leukemia," 2000.

"Cloning of DNA Sequences from the White Locus of *D. melanogaster* by a Novel and General Method," *Cell*, Sep. 1981, pp. 693-704, vol. 25.

E.L. Pugh et al., "Studies of the Mechanism of Fatty Acid Synthesis," *The Journal of Biological Chemistry*, Dec. 1965, vol. 240, No. 12.

Devin O'Hare, "DNA Sequence of the White Locus of *Drosophila melanogaster*," *J. Mol. Biol.*, pp. 437-455, vol. 180.

"Camptothecin Resistance: Role of the ATP-binding Cassette (ABC), Mitoxantrone-Resistance Half Transporter (MXR), and Potential for Glucuronidation in MXR-expressing Cells," *Cancer Research*, Dec. 1, 1999, pp. 5938-5946, vol. 59.

June L. Biedler et al., "Cellular Resistance to Actinomycin D in Chinese Hamster Cells in Vitro: Cross Resistance, Radioautographic and Cytogenetic Studies," *Cancer Research*, Apr. 1970, pp. 1174-1184, vol. 30.

Craig R. Fairchild et al., "Isolation of Amplified and Overexpressed DNA Sequences from Adriamycin-Resistant Human Breast Cancer Cells," *Cancer Research*, Oct. 1, 1987, pp. 5141-5148, vol. 47.

W. Grzydon Harker et al., "Multidrug Resistance in Mitoxantrone-Selected HL-60 Leukemia Cells in the Absence of P-Glycoprotein Overexpression," *Cancer Research*, Aug. 15, 1989, pp. 4542-4549, vol. 49.

Philip Skehan et al., "New Colorimetric Cytotoxicity Assay for Anticancer-Drug Screening," *J. National Cancer Institute*, Jul. 14, 1990, vol. 82, No. 13.

G. Kohler et al., "Derivation of Specific Antibody-Producing Tissue Culture and Tumor Lines by Cell Fusion," *Eur. J. Immunol.*, 1976, pp. 511-519, vol. 6.

Peng Liang et al., "Differential Display and Cloning of Messenger RNAs from Human Breast Cancer Versus Mammary Epithelial Cells," *Cancer Research*, Dec. 15, 1992, pp. 6966-6968, vol. 52.

Victor Ling, "Reduced Permeability in CHO Cells as a Mechanism of Resistance to Colchicine," *J. Cell Physiol.*, pp. 103-116, vol. 83.

G. Kohler, "Fusion Between Immunoglobuline-Secreting and Nonsecreting Myeloma Cell Lines," *Eur. J. Immunol.*, 1976, pp. 292-295, vol. 6.

Peng Liang et al., "Differential Display of Eukaryotic Messenger RNA by Means of the Polymerase Chain Reaction," *Science*, Aug. 14, 1992, pp. 967-971, vol. 257.

"Sequence of a cDNA from the *Drosophila melanogaster* White Gene," *Nucleic Acids Research*, Feb. 20, 1990, pp. 1633, vol. 18, No. 6.

G. Kohler, "Continuous Cultures of Fused Cells Secreting Antibody of Predefined Specificity," *Nature*, Aug. 7, 1975, vol. 256.

Hitoshi Kawaharata et al., "Decreased Sensitivity of Carcinoembryonic Antigen cDNA-Transfected Cells to Adriamycin," *Int. J. Cancer*, 1997, pp. 377-382, vol. 72.

Qiang Yu et al., "Two COOH-Terminal Truncated Ctoplasmic Forms of Topoisomerase II in a VP-16-Selected Lung Cancer Cell Line Results from Partial Gene Deletion and Alternative Splicing," *Biochemistry*, 1997, pp. 5868-5877, vol. 37.

L. Austin et al., "H19 Gene Overexpression in Atypical Multi-drug-Resistant Cells Associated with Expression of a 95-Kilodalton Membrane Glycoprotein," *Cancer Research*, Jul. 1, 1996, pp. 2904-2904, vol. 56.

L. Austin Doyle et al., "A Multidrug Resistance Transporter Form Human MCF-7 Breast Cancer Cells," *Medical Sciences*, Dec. 1998, pp. 15665-15670, vol. 95, Proc. Natl. Acad. Sci. USA.

Rando Allikmets et al., "A Human Placenta-Specific ATP-Binding Cassette Gene (ABCP) on Chromosome 4q22 That Is Involved in Multidrug Resistance," *Cancer*, Dec. 1, 1998, pp. 5337-5339.

Keisuke Miyake et al., "Molecular Cloning of cDNAs Which Are Highly Overexpressed in Mitoxantrone Resistant Cells: Demonstration of Homology to ABC Transport Genes," *Cancer Research*, Jan. 1, 1999, pp. 8-13, vol. 59.

Ken Taniguchi et al., "A Human Canalicular Multispecific Organic Anion Transporter (cMOAT) Gene Is Overexprssed in Cisplantin-Resistant Human Cancer Cell Lines with Decreased Drug Accumulation," *Cancer Research*, Sep. 15, 1996, pp. 4124-4129, vol. 56.

Haiming Chen et al., "Cloning of the cDNA for a Human Homoloromosome 21q22.3gue of the *Drosophila* White Gene and Mapping to Chromosome 21q22.3," *Am. J. Genet.*, 1996, pp. 66-75, vol. 59.

T Gura, "Antisense Has Growing Pains," *Science*, Oct. 27, 1995, pp. 575-577, vol. 270.

James et al., *Science*, Mar. 16, 1990, pp. 1300-1310, vol. 247.

Eliane Lazar et al., "Transforming Growth Factor α: Mutation of Aspartic Acid 47 and Leucine 48 Results in Different Biological Activities," *Molecular and Cellular Biology*, Mar. 1988, pp. 1247-1252, vol. 8, No. 3.

Wilson H. Burgess et al., *The Journal of Cell Biology*, Nov. 1990, pp. 2129-2138, vol. 111.

Hillier et al. (W84773), GenBank Sequence Database (Accession W84357), 1995 Ntl. Ctr. For Biotech. Info., Natl. Lib. Medicine, Bethesda, MD.

Chang-Jie Chen et al., "Genomic Organization of the Human Multidrug Resistance (MDR1) Gene and Origin of P-glycoproteins," *The Journal of Biological Chemistry*, 1999, pp. 506-514, vol. 265(1).

A. Austin Doyle et al., "Characterization of a 95 Kilodalton Membrane Glycoprotein Associated with Multi-Drug Resistance," *Int. J. Cancer*, 1995, pp. 593-598, vol. 62.

L.A. Doyle et al., "Expression of a 95 kDa Membrane Protein is Associated with Low Daunorubicin Accumulation in Leukaemic Blast Cells," *Br. J. Cancer*, Jan. 1995, pp. 52-58, vol. 71(1).

D.D. Ross et al., "Expression of Multidrug Resistance-Associated Protein (MRP) mRNA in Blast Cells from Acute Myeloid Leukemia (AML) Patients," *Leukemia*, 1996, pp. 48-55, vol. 10.

D.D. Ross et al., "Susceptibility of Idarubincin, Daunorubicin and Their C-13 Alcohol Metabolites to Transport-Mediated Multidrug Resistance," *Biochemical Pharmacology*, 1995, pp. 1673-1683, vol. 50(10).

Purnelle et al. (GenBank, Sequence Database Accession P25371), National Center for Biotechnology Information, National Library of Medicine, Bethda MD, publicly available May 1, 2001.

Kirby et al. (GenBank, Sequence Database Accession Q94960), National Center for Biotechnology Information, National Library of Medicine, Bethda MD, publicly available Feb. 1, 1997.

Roitt et al. *Immunology*, 1993, pp. 6.4-6.5, Mosby, St. Louis.

Herbert et al., *The Dictionary of Immunology*, 1985, pp. 58-59, 4th Edition, Academic Press.

Oches, "Autoantibodies in Breast Cancer," electronic reference at http://www.cbcrp.org/research/PageGrant.asp?grant_id=198.

L. Hillier et al., "Generation and Analysis of 280,000 Humana Expressed Sequence Tags," *Genome Research*, 1996, pp. 807-828, vol. 6(9).

Jaroszewski et al., "Concerning Antisense Inhibition of the Multiple Drug Resistance Gene," *Cancer Communications*, 1990, pp. 287-294, vol. 2(8).

Yang et al., "Cloning and Characterization of Breast Cancer Resistance Protein (BCRP), A Novel ATP-Binding Cassette (ABC) Transporter That May Contribute to the Multi-drug Resistance Phenotype of MCF-7/ADRVP Breast Cancer Cells," *Proceedings of the 89th Annual Meeting of the American Association for Cancer Research*, 1998, (abstract), vol. 39:657.

Dexter et al., Proc. AACR, 1996, 37:A2138.

Harlow et al., Antibodies: A Laboratory Manual, 1988, p. 142, Cold Spring Harbor Laboratory Press.

Bowie et al., "Deciphering the Message in Protein Sequences: Tolerance to Amino Acid Substitutions," *Science*, 1990, pp. 1306-1310, vol. 247.

Filipits et al., "MRP and MDR1 Gene Expression in Primary Breast Carcinomas," *Clinical Cancer Research*, Jul. 1996, 2:1231-1237, Abstract only.

Polynucleotide Sequence Genbank Accession No. U66681 (GI:1906566).

Polypeptide Sequence Genbank Accession No. AAC97367 (GI:4038352).

Ross, D.D.; Doyle, L.A.; Hazlehurst, L.A.; Yang, W.; Greenberg, L.W.; Hacker, M.; Abruzzo, L.V.; Dalton, W.S.; Mitoxantrone-resistant human 8226 myeloma cells overexpress breast cancer resistance protein (BCRP); Blood Nov. 15, 1998;92(10 Supp 1 Pt 1):676a. The data were presented at the conference "The American Society of Hematology 40th Annual Meeting" held on Dec. 4-8, 1998, in Miami Beach, Florida, USA (abstract # 2785).

Ross, D.D.; Karp J.; Yang, W.; Gao, Y.; Abruzzo, L.V.; Doyle, L.A.; Expression of breast cancer resistant protein (BCRP) in blast cells from patients with acute myeloid leukemia (AML); Blood Nov. 15, 1998;92(10 Supp 1 Pt 1):386a. The data were presented at the conference "The American Society of Hematology 40th Annual Meeting" held on Dec. 4-8, 1998, in Miami Beach, Florida, USA (abstract # 1595).

Doyle LA, Yang W, Abruzzo LE, Krogmann T, Gao Y, Rishi AK, Ross DD. Cloning and characterization of breast cancer resistance protein (BCRP), a novel ATP-binding cassette (ABC) transporter that may contribute to the multidrug-resistance phenotype of MCF-7/AdrVp breast cancer cells; Proceedings of the American Association for Cancer Research Annual Meeting Mar. 1998; 39:657. The data were presented at the conference "89th Annual Meeting of the American Association for Cancer Research" held on Mar. 28-Apr. 1, 1998, New Orleans LA, USA (abstract #4475).

Sequence alignment of SEQ ID No. 2 and EST 157481.

Sequence alignment of SEQ ID No. 1 and AAC97367,1.

Stryer, L. *Biochemie*, Chapter 35 "Molekulare Immunologie", p. 925-933, Korr. Nachdruck 1991, Heidelberg (Spektrum Akademischer Verlag) 1991.

Watson, D. *Rekombinierte DNA*, Chapter 12, p. 209-210, 2. Auflage, Heidelberg (Spektrum Akademischer Verlag) 1993.

Stryer, L. *Biochemie*, last page, table "Der genetische Standartcode", Korr. Nachdruck 1991, Heidelberg (Spektrum Akademischer Verlag) 1991.

European Opposition to European Patent No. 1054894.

* cited by examiner

```
  1 MSSSNVEVFI PVSQGNTNGF PATASNDLKA FTEGAVLSFH NICYRVKLKS
                                      WALKER A MOTIF
 51 GFLPCRKPVE KEILSNINGI MKPGLNAILG PTGGGKSSLL DVLAARKDPS

101 GLSGDVLING APRPANFKCN SGYVVQDDVV MGTLTVRENL QFSAALRLAT

151 TMTNHEKNER INRVIQELGL DKVADSKVGT QFIRGVSGGE RKRTSIGMEL
                   PHOSPHOPANTETHEINE SITE
201 ITDPSILFLD EPTTGLDSST ANAVLLLKR MSKQGRTIIF SIHQPRYSIF

251 KLFDSLTLLA SGRLMFHGPA QEALGYFESA GYHCEAYNNP ADFFLDIING
                                                GLYC
301 DSTAVALNRE EDFKATEIIE PSKQDKPLIE KLAEIYVNSS FYKETKAELH

351 QLSGGEKKKK ITVFKEISYT TSFCHQLRWV SKRSFKNLLG NPQASIAQII
                                                  ←
                         GLYC
401 VTVVLGLVIG AIYFGLKNDS TGIQNRAGVL FFLTTNQCFS SVSAVELFVV
    ————→
     TM 1
451 EKKLFIHEYI SGYYRVSSYF LGKLLSDLLP MTMLPSIIFT CIVYFMLGLK

501 PKADAFFVMM FTLMMVAYSA SSMALAIAAG QSVVSVATLL MTICFVFMMI
          GLYC                                          GLYC
551 FSGLIVNLTT IASWLSWLQY FSIPRYGFTA LQHNEFLGQN FCPGLNATGN
    ——→
    TM 2
601 NPCNYATCTG EEYLVKQGID LSPWGLWKNH VALACMIVIF LTIAYLKLLF
                                    ←————  ————→
                                          TM 3
651 LKKYS
```

FIG. 2A

```
  1  GGGAGGAGGC AGCCTGTGGA GGAACTGGGT AGGATTTAGG AACGCACCGT
 51  GCACATGCTT GGTGGTCTTG TTAAGTGGAA ACTGCTGCTT TAGAGTTTGT
101  TTGGAAGGTC CGGGTGACTC ATCCCAACAT TTACATCCTT AATTGTTAAA
151  GCGCTGCCTC CGAGCGCACG CATCCTGAGA TCCTGAGCCT TTGGTTAAGA
201  CCGAGCTCTA TTAAGCTGAA AAGATAAAAA CTCTCCAGAT GTCTTCCAGT
251  AATGTCGAAG TTTTTATCCC AGTGTCACAA GGAAACACCA ATGGCTTCCC
301  CGCGACAGCT TCCAATGACC TGAAGGCATT TACTGAAGGA GCTGTGTTAA
351  GTTTTCATAA CATCTGCTAT CGAGTAAAAC TGAAGAGTGG CTTTCTACCT
401  TGTCGAAAAC CAGTTGAGAA AGAAATATTA TCGAATATCA ATGGGATCAT
451  GAAACCTGGT CTCAACGCCA TCCTGGGACC CACAGGTGGA GGCAAATCTT
501  CGTTATTAGA TGTCTTAGCT GCAAGGAAAG ATCCAAGTGG ATTATCTGGA
551  GATGTTCTGA TAAATGGAGC ACCGCGACCT GCCAATTTCA AATGTAATTC
601  AGGTTACGTG GTACAAGATG ATGTTGTGAT GGGCACTCTG ACGGTGAGAG
651  AAAACTTACA GTTCTCAGCA GCTCTTCGGC TTGCAACAAC TATGACGAAT
701  CATGAAAAAA ACGAACGGAT TAACAGGGTC ATTCAAGAGT TAGGTCTGGA
751  TAAAGTGGCA GACTCCAAGG TTGGAACTCA GTTTATCCGT GGTGTGTCTG
801  GAGGAGAAAG AAAAAGGACT AGTATAGGAA TGGAGCTTAT CACTGATCCT
851  TCCATCTTGT TCTTGGATGA GCCTACAACT GGCTTAGACT CAAGCACAGC
```

FIG. 2C-1

```
 901    AAATGCTGTC CTTTTGCTCC TGAAAAGGAT GTCTAAGCAG GGACGAACAA
 951    TCATCTTCTC CATTCATCAG CCTCGATATT CCATCTTCAA GTTCTTTGAT
1001    AGCCTCACCT TATTGGCCTC AGGAAGACTT ATGTTCCACG GGCTGCTCA
1051    GGAGGCCTTG GGATACTTTG AATCAGCTGG TTATCACTGT GAGGCCTATA
1101    ATAACCCTGC AGACTTCTTC TTGGACATCA TTAATGGAGA TTCCACTGCT
1151    GTGGCATTAA ACAGAGAAGA AGACTTTAAA GCCACAGAGA TCATAGAGCC
1201    TTCCAAGCAG GATAAGCCAC TCATAGAAAA ATTAGCGGAG ATTTATGTCA
1251    ACTCCTCCTT CTACAAAGAG ACAAAAGCTG AATTACATCA ACTTTCCGGG
1301    GGTGAGAAGA AGAAGAAGAT CACGGTCTTC AAGGAGATCA GCTACACCAC
1351    CTCCTTCTGT CATCAACTCA GATGGGTTTC CAAGCGTTCA TTCAAAAACT
1401    TGCTGGGTAA TCCCCAGGCC TCTATAGCTC AGATCATTGT CACAGTCGTA
1451    CTGGGACTGG TTATAGGTGC CATTTACTTT GGGCTAAAAA ATGATTCTAC
1501    TGGAATCCAG AACAGAGCTG GGGTTCTCTT CTTCCTGACG ACCAACCAGT
1551    GTTTCAGCAG TGTTTCAGCC GTGGAACTCT TTGTGGTAGA GAAGAAGCTC
1601    TTCATACATG AATACATCAG CGGATACTAC AGAGTGTCAT CTTATTTCCT
1651    TGGAAAACTG TTATCTGATT TATTACCCAT GACGATGTTA CCAAGTATTA
                                         5' 1727       1744
1701    TATTTACGTG TATAGTGTAC TTCATGTTAG GATTGAAGCC AAAGGCAGAT
                                        5' PCR PRIMER (SENSE)
1751    GCCTTCTTCG TTATGATGTT TACCCTTATG ATGGTGGCTT ATTCAGCCAG
1801    TTCCATGGCA CTGGCCATAG CAGCAGGTCA GAGTGTGGTT TCTGTAGCAA
```

FIG. 2C-2

| | |
|---|---|
| 1851 | CACTTCTCAT GACCATCTGT TTTGTGTTTA TGATGATTTT TTCAGGTCTG |
| 1901 | TTGGTCAATC TCACAACCAT TGCATCTTGG CTGTCATGGC TTCAGTACTT |
| 1951 | CAGCATTCCA CGATATGGAT TTACGGCTTT GCAGCATAAT GAATTTTTGG |
| 2001 | GACAAAACTT CTGCCCAGGA CTCAATGCAA CAGGAAACAA TCCTTGTAAC |
| 2051 | TATGCAACAT GTACTGGCGA AGAATATTTG GTAAAGCAGG GCATCGATCT |
| 2101 | CTCACCCTGG GGCTTGTGGA AGAATCACGT GGCCTTGGCT TGTATGATTG |
| 2151 | T TATTTTCCT CACAATTGCC TA CCTGAAAT TGTTATTTCT TAAAAAATAT |
| 2201 | TCTTAAATTT CCCCTTAATT CAGTATGATT TATCCTCACA TAAAAAAGAA |
| 2251 | GCACTTTGAT TGAAGTATTC AATCAAGTTT TTTTGTTGTT TTCTGTTCCC |
| 2301 | TTGCCATCAC ACTGTTGCAC AGCAGCAATT GTTTAAAGA GATACATTTT |
| 2351 | TAGAAATCAC AACAAACTGA ATTAAACATG AAAGAACCCA AAAAAAAGA |
| 2401 | TATCACTCAG CATAATGA |

| CELL LINE | MITOZANTRONS | | DAUNORUBICIN | | DEXPRUBICIN | | IDARUBICIN | | CIAPLATIN | | PACLITAXEL | |
|---|---|---|---|---|---|---|---|---|---|---|---|---|
| | LC50 | RF | LC50 | RF | LC50 | RF | LC50 | RF | LC50 | RF | LC50 | RF |
| MCF-7/W | 48 | 1.0 | 47 | 1.0 | 57 | 1.0 | 75 | 1.0 | 2,367 | 1.0 | 1.9 | 1.0 |
| MCF-7/pcDNA3 | 54 | 1.1 | 72 | 1.5 | 66 | 1.2 | 126 | 1.7 | 3,525 | 1.5 | 3.0 | 1.6 |
| MCF-7/BCRPc19 | 21 | 0.4 | 54 | 1.1 | 67 | 1.2 | 107 | 1.4 | 8,950 | 2.9 | 0.8 | 0.4 |
| MCF-7/BCRPall | 393** | 8.2 | 218** | 4.5 | 254 | 5.2 | 140 | 1.8 | 3,080 | 1.3 | 1.4 | 0.7 |
| MCF-7/BCRPcS | 1,495** | 31.2 | 328** | 7.0 | 768* | 9.2 | 285 | 3.5 | 3,700 | 1.6 | 1.8 | 0.9 |
| MCF-7/AdrVp | 180,000** | 3333 | 1667** | 35.5 | 8650** | 175.0 | 70 | 0.8 | 4,700 | 2.01 | 2.8 | 1.5 |

\* = DIFFERS SIGNIFICANTLY FROM MCF-7/W OR MCF-7/pcDNA3, $p < 0.05$ (STUDENT'S t TEST)
\** = DIFFERS SIGNIFICANTLY FROM MCF-7/W OR MCF-7/pcDNA3, $p < 0.01$ (STUDENT'S t TEST)

FIG. 5

SEQUENCE LISTING

<160> NUMBER OF SEQ ID NOS: 7

<210> SEQ ID NO 1
<211> LENGTH: 655
<212> TYPE: PRT
<213> ORGANISM: Homo sapiens

<400> SEQUENCE: 1

```
Met Ser Ser Asn Val Glu Val Phe Ile Pro Val Ser Gln Gly Asn
 1               5                  10                  15

Thr Asn Gly Phe Pro Ala Thr Ala Ser Asn Asp Leu Lys Ala Phe Thr
                 20                  25                  30

Glu Gly Ala Val Leu Ser Phe His Asn Ile Cys Tyr Arg Val Lys Leu
             35                  40                  45

Lys Ser Gly Phe Leu Pro Cys Arg Lys Pro Val Glu Lys Glu Ile Leu
     50                  55                  60

Ser Asn Ile Asn Gly Ile Met Lys Pro Gly Leu Asn Ala Ile Leu Gly
 65                  70                  75                  80

Pro Thr Gly Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
            115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
            195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
            275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350
```

```
Ser Gly Gly Glu Lys Lys Lys Ile Thr Val Phe Lys Glu Ile Ser
        355                 360                 365
Tyr Thr Thr Ser Phe Cys His Gln Leu Arg Trp Val Ser Lys Arg Ser
    370                 375                 380
Phe Lys Asn Leu Leu Gly Asn Pro Gln Ala Ser Ile Ala Gln Ile Ile
385                 390                 395                 400
Val Thr Val Val Leu Gly Leu Val Ile Gly Ala Ile Tyr Phe Gly Leu
                405                 410                 415
Lys Asn Asp Ser Thr Gly Ile Gln Asn Arg Ala Gly Val Leu Phe Phe
            420                 425                 430
Leu Thr Thr Asn Gln Cys Phe Ser Ser Val Ser Ala Val Glu Leu Phe
        435                 440                 445
Val Val Glu Lys Lys Leu Phe Ile His Glu Tyr Ile Ser Gly Tyr Tyr
    450                 455                 460
Arg Val Ser Ser Tyr Phe Leu Gly Lys Leu Leu Ser Asp Leu Leu Pro
465                 470                 475                 480
Met Thr Met Leu Pro Ser Ile Ile Phe Thr Cys Ile Val Tyr Phe Met
                485                 490                 495
Leu Gly Leu Lys Pro Lys Ala Asp Ala Phe Phe Val Met Met Phe Thr
            500                 505                 510
Leu Met Met Val Ala Tyr Ser Ala Ser Ser Met Ala Leu Ala Ile Ala
        515                 520                 525
Ala Gly Gln Ser Val Val Ser Val Ala Thr Leu Leu Met Thr Ile Cys
    530                 535                 540
Phe Val Phe Met Met Ile Phe Ser Gly Leu Leu Val Asn Leu Thr Thr
545                 550                 555                 560
Ile Ala Ser Trp Leu Ser Trp Leu Gln Tyr Phe Ser Ile Pro Arg Tyr
                565                 570                 575
Gly Phe Thr Ala Leu Gln His Asn Glu Phe Leu Gly Gln Asn Phe Cys
            580                 585                 590
Pro Gly Leu Asn Ala Thr Gly Asn Asn Pro Cys Asn Tyr Ala Thr Cys
        595                 600                 605
Thr Gly Glu Glu Tyr Leu Val Lys Gln Gly Ile Asp Leu Ser Pro Trp
    610                 615                 620
Gly Leu Trp Lys Asn His Val Ala Leu Ala Cys Met Ile Val Ile Phe
625                 630                 635                 640
Leu Thr Ile Ala Tyr Leu Lys Leu Leu Phe Leu Lys Lys Tyr Ser
                645                 650                 655

<210> SEQ ID NO 2
<211> LENGTH: 2418
<212> TYPE: DNA
<213> ORGANISM: Homo sapiens

<400> SEQUENCE: 2
gggaggaggc agcctgtgga ggaactgggt aggatttagg aacgcaccgt gcacatgctt      60
ggtggtcttg ttaagtggaa actgctgctt tagagtttgt ttggaaggtc cgggtgactc     120
atcccaacat ttacatcctt aattgttaaa gcgctgcctc cgagcgcacg catcctgaga     180
tcctgagcct ttggttaaga ccgagctcta ttaagctgaa aagataaaaa ctctccagat     240
gtcttccagt aatgtcgaag tttttatccc agtgtcacaa ggaaacacca atggcttccc     300
cgcgacagct tccaatgacc tgaaggcatt tactgaagga gctgtgttaa gttttcataa     360
catctgctat cgagtaaaac tgaagagtgg cttttctacct tgtcgaaaac cagttgagaa     420
```

-continued

| | |
|---|---|
| agaaatatta tcgaatatca atgggatcat gaaacctggt ctcaacgcca tcctgggacc | 480 |
| cacaggtgga ggcaaatctt cgttattaga tgtcttagct gcaaggaaag atccaagtgg | 540 |
| attatctgga gatgttctga taaatggagc accgcgacct gccaatttca aatgtaattc | 600 |
| aggttacgtg gtacaagatg atgttgtgat gggcactctg acggtgagag aaaacttaca | 660 |
| gttctcagca gctcttcggc ttgcaacaac tatgacgaat catgaaaaaa acgaacggat | 720 |
| taacagggtc attcaagagt taggtctgga taaagtggca gactccaagg ttggaactca | 780 |
| gtttatccgt ggtgtgtctg gaggagaaag aaaaaggact agtataggaa tggagcttat | 840 |
| cactgatcct tccatcttgt tcttggatga gcctacaact ggcttagact caagcacagc | 900 |
| aaatgctgtc cttttgctcc tgaaaaggat gtctaagcag ggacgaacaa tcatcttctc | 960 |
| cattcatcag cctcgatatt ccatcttcaa gttgtttgat agcctcacct tattggcctc | 1020 |
| aggaagactt atgttccacg ggcctgctca ggaggccttg ggatactttg aatcagctgg | 1080 |
| ttatcactgt gaggcctata ataccctgc agacttcttc ttggacatca ttaatggaga | 1140 |
| ttccactgct gtggcattaa acagagaaga agactttaaa gccacagaga tcatagagcc | 1200 |
| ttccaagcag gataagccac tcatagaaaa attagcggag attatgtca actcctcctt | 1260 |
| ctacaaagag acaaaagctg aattacatca actttcgggg ggtgagaaga agaagaagat | 1320 |
| cacggtcttc aaggagatca gctacaccac ctccttctgt catcaactca gatgggtttc | 1380 |
| caagcgttca ttcaaaaact tgctgggtaa tccccaggcc tctatagctc agatcattgt | 1440 |
| cacagtcgta ctgggactgg ttataggtgc catttacttt gggctaaaaa atgattctac | 1500 |
| tggaatccag aacagagctg gggttctctt cttcctgacg accaaccagt gtttcagcag | 1560 |
| tgtttcagcc gtggaactct tgtggtagaa gaagaagctc ttcatacatg aatacatcag | 1620 |
| cggatactac agagtgtcat cttatttcct tggaaaactg ttatctgatt tattacccat | 1680 |
| gacgatgtta ccaagtatta tatttacctg tatagtgtac ttcatgttag gattgaagcc | 1740 |
| aaaggcagat gccttcttcg ttatgatgtt taccctttatg atggtggctt attcagccag | 1800 |
| ttccatggca ctggccatag cagcaggtca gagtgtggtt tctgtagcaa cacttctcat | 1860 |
| gaccatctgt tttgtgttta tgatgatttt ttcaggtctg ttggtcaatc tcacaaccat | 1920 |
| tgcatcttgg ctgtcatggc ttcagtactt cagcattcca cgatatggat ttacggcttt | 1980 |
| gcagcataat gaatttttgg gacaaaaactt ctgcccagga ctcaatgcaa caggaaacaa | 2040 |
| tccttgtaac tatgcaacat gtactggcga agaatatttg gtaaagcagg gcatcgatct | 2100 |
| ctcaccctgg ggcttgtgga agaatcacgt ggccttggct tgtatgattg ttattttcct | 2160 |
| cacaattgcc tacctgaaat tgttatttct taaaaaatat tcttaaattt ccccttaatt | 2220 |
| cagtatgatt tatcctcaca taaaaaagaa gcactttgat tgaagtattc aatcaagttt | 2280 |
| ttttgttgtt ttctgttccc ttgccatcac actgttgcac agcagcaatt gttttaaaga | 2340 |
| gatacatttt tagaaatcac aacaaactga attaaacatg aaagaaccca aaaaaaaaga | 2400 |
| tatcactcag cataatga | 2418 |

<210> SEQ ID NO 3
<211> LENGTH: 16
<212> TYPE: DNA
<213> ORGANISM: Homo sapiens

<400> SEQUENCE: 3

| | |
|---|---|
| cgaccgacga cacaga | 16 |

```
<210> SEQ ID NO 4
<211> LENGTH: 21
<212> TYPE: DNA
<213> ORGANISM: Homo sapiens

<400> SEQUENCE: 4
cttaaaatga atgcgattga t                                              21

<210> SEQ ID NO 5
<211> LENGTH: 19
<212> TYPE: DNA
<213> ORGANISM: Homo sapiens

<400> SEQUENCE: 5
ttaggattga agccaaagg                                                 19

<210> SEQ ID NO 6
<211> LENGTH: 21
<212> TYPE: DNA
<213> ORGANISM: Homo sapiens

<400> SEQUENCE: 6
taggcaattg tgaggaaaat a                                              21

<210> SEQ ID NO 7
<211> LENGTH: 795
<212> TYPE: DNA
<213> ORGANISM: Homo sapiens

<400> SEQUENCE: 7
tcattatgct gagtgatatc ttttttttg gaaaactgtt atctgattta ttacccatga      60
cgatgttacc aagtattata tttacctgta tagtgtactt catgttagga ttgaagccaa    120
aggcagatgc cttcttcgtt atgatgttta cccttatgat ggtggcttat tcagccagtt   180
ccatggcact ggccatagca gcaggtcaga gtgtggtttc tgtagcaaca cttctcatga   240
ccatctgttt tgtgtttatg atgattttt caggtctgtt ggtcaatctc acaaccattg    300
catcttggct gtcatggctt cagtacttca gcattccacg atatggattt acggctttgc   360
agcataatga attttggga caaaacttct gcccaggact caatgcaaca ggaaacaatc    420
cttgtaacta tgcaacatgt actggcgaag aatatttggt aaagcagggc atcgatctct   480
caccctgggg cttgtggaag aatcacgtgg ccttggcttg tatgattgtt attttcctca   540
caattgccta cctgaaattg ttatttctta aaaaatattc ttaaatttcc ccttaattca    600
gtatgattta tcctcacata aaaagaagc actttgattg aagtattcaa tcaagttttt   660
ttgttgtttt ctgttccctt gccatcacac tgttgcacag cagcaattgt tttaaagaga    720
tacattttta gaaatcacaa caaactgaat taaacatgaa agaacccaaa aaaaaagata   780
tcactcagca taatg                                                    795
```

BREAST CANCER RESISTANCE PROTEIN (BCRP) AND THE DNA WHICH ENCODES IT

This application is a division of U.S. patent application Ser. No. 09/961,086 filed Sep. 21, 2001, which is a division of U.S. patent application Ser. No. 09/245,808 filed Feb. 5, 1999, now U.S. Pat. No. 6,313,277, which claims priority under 35 U.S.C. § 119(e) to U.S. Provisional Application No. 60/073,763 filed Feb. 5, 1998.

This application is based upon U.S. Provisional 60/073,763, filed Feb. 5, 1998.

STATEMENT OF FEDERALLY SPONSORED RESEARCH AND DEVELOPMENT

This invention was made with government support under Grant No. CA52178 awarded by NIH. The government has certain rights in the invention.

FIELD OF THE INVENTION

The invention relates to the family of proteins known as multidrug resistance proteins. These proteins are xenobiotic transporters which confer resistance to cancer chemotherapeutic drugs. The invention describes a new protein member of this family called Breast Cancer Resistance Protein (BCRP) and the DNA which encodes it.

BACKGROUND OF THE INVENTION

The development of resistance to multiple chemotherapeutic drugs frequently occurs during the treatment of cancer. Two transmembrane xenobiotic transporter proteins, P-glycoprotein (Pgp) and the multidrug resistance protein (MRP) are capable of causing multidrug resistance when transfected into drug-sensitive cells in culture (1,2). Despite this, the role that these transporters play in clinical drug resistance exhibited by human cancers is unclear, and alternate or additional drug resistance mechanisms operative in this disease have been sought.

To address this problem, Chen et. al. (3) selected human breast carcinoma MCF-7 cells for resistance to the anthracycline doxorubicin in the presence of verapamil, an inhibitor of Pgp. The resultant multidrug resistant subline, MCF-7/AdrVp, exhibits marked cross-resistance to other anthracyclines (daunorubicin [DNR], 3'-deamino-3'[3-cyano-4-morpholinyl]doxorubicin, but not idarubicin), and to the anthracenedione mitoxantrone, but remains sensitive to vinca alkaloids, paclitaxel (3,4) and cisplatin. MCF-7/AdrVp cells do not overexpress Pgp or MRP, despite displaying a marked reduction in the intracellular accumulation of the anthracycline daunorubicin and the fluorescent dye rhodamine 123 compared to MCF-7 cells (4,5). MCF-7/AdrVp cells do not display an alteration in the subcellular distribution of drug (4) such as that seen in certain cells that overexpress MRP. Although the decreased accumulation of daunorubicin in MCF-7/AdrVp cells is not reversed by the classical P-glycoprotein antagonist cyclosporin A, depletion of ATP results in complete abrogation of the abnormal efflux of both daunorubicin and rhodamine (4).

The need in the art to elucidate the mechanism of drug resistance is continually present, as chemotherapy remains the primary method for non-invasively treating many types of cancers. There is also a need in the art to counteract the mechanism of drug resistance so to provide a longer and more effective course of chemotherapeutic drug treatment for cancer patients.

SUMMARY OF THE INVENTION

The discovery described in the instant invention fulfills the above needs. The discovery of the BCRP and its corresponding gene greatly advance the knowledge in the art of the drug resistance mechanism by providing a novel xenobiotic transporter which is overexpressed in a variety of drug-resistant human cancer cell lines, and confers resistance to many chemotherapeutic agents.

BCRP is an about 655 amino acid protein and is encoded by a gene which has about 2418 nucleotide cDNA. The protein demonstrates activity and has a sequence homology which places it in the ATP-binding cassette (ABC) superfamily of transporter proteins. The molecular mass is approximately 72.3 kilodaltons (kD) exclusive of any glycoylation. Expression of BCRP in drug-sensitive human cancer cells confers resistance to mitoxantrone, doxorubicin, and daunorubicin, and reduces daunorubicin accumulation in the cloned transfected cells.

It is an object of the present invention to provide a mammalian protein that is a multi-drug resistant (MDR) protein and a xenobiotic transporter, and is called Breast Cancer Resistance Protein (BCRP).

It is also an object of the present invention is to provide the gene and/or cDNA which encodes said mammalian MDR protein.

It is another object of the invention to provide antisense fragments of the BCRP gene which inhibit the expression of the BCRP in vivo.

Yet another object of the present invention is to provide a method of using probes derived from the BCRP gene as a diagnostic tool to quantify gene expression or gene amplification in specimens taken from patients with cancer.

It is another object of the invention to provide antibodies to the BCRP.

It is yet another object of the invention to provide a method of reversing the drug resistance of the cancer cells by administering BCRP antibodies.

It is yet another object of the invention to provide a method of reversing the drug resistance of the cancer cells by administering Fumitremorgin C.

It is another object of the invention to provide a method of enhancing a patient's chemotherapy treatment for breast cancer by administering antibodies to the patient to inhibit the resistance-activity of BCRP.

These and other objects of the present invention, which will be apparent from the detailed description of the invention provided hereinafter, have been met, in one embodiment, by substantially pure BCRP and the gene encoding BCRP.

BRIEF DESCRIPTION OF THE DRAWINGS

FIG. 2A is the deduced amino acid sequence of BCRP [SEQ ID NO. 1] with motifs.

FIG. 2C, comprising FIGS. 2C-1, 2C-2 and 2C-3, is the cDNA sequence [SEQ ID NO. 2] which encodes the BCRP.

FIG. 3 shows an autoradiograph of a multiple tissue Northern blot. Key to the lane numbering is as follows: heart (1), brain (2), placenta (3), lung (4), liver (5), skeletal muscle (6), kidney (7), pancreas (8), spleen (9), thymus (10), prostate (11), testis (12), ovary (13), small intestine (14), colon (15), peripheral blood leukocytes (16).

FIG. 4D, comprising FIGS. 4D-1 through 4D-6, are graphs showing the effect of various chemotherapeutic drugs' concentrations on BCRP-transfected MCF-7 clone 8 cell survival.

FIG. 5 is a table showing the effect of various chemotherapeutic drugs on BCRP-transfected MCF-7 cells.

FIG. 6 is an autoradiograph showing the expression of Human w gene in MCF-7 cells detected by the Reverse Transcription-Polymerase chain reaction (RT-PCR).

DETAILED DESCRIPTION OF THE INVENTION

Figure 1A:
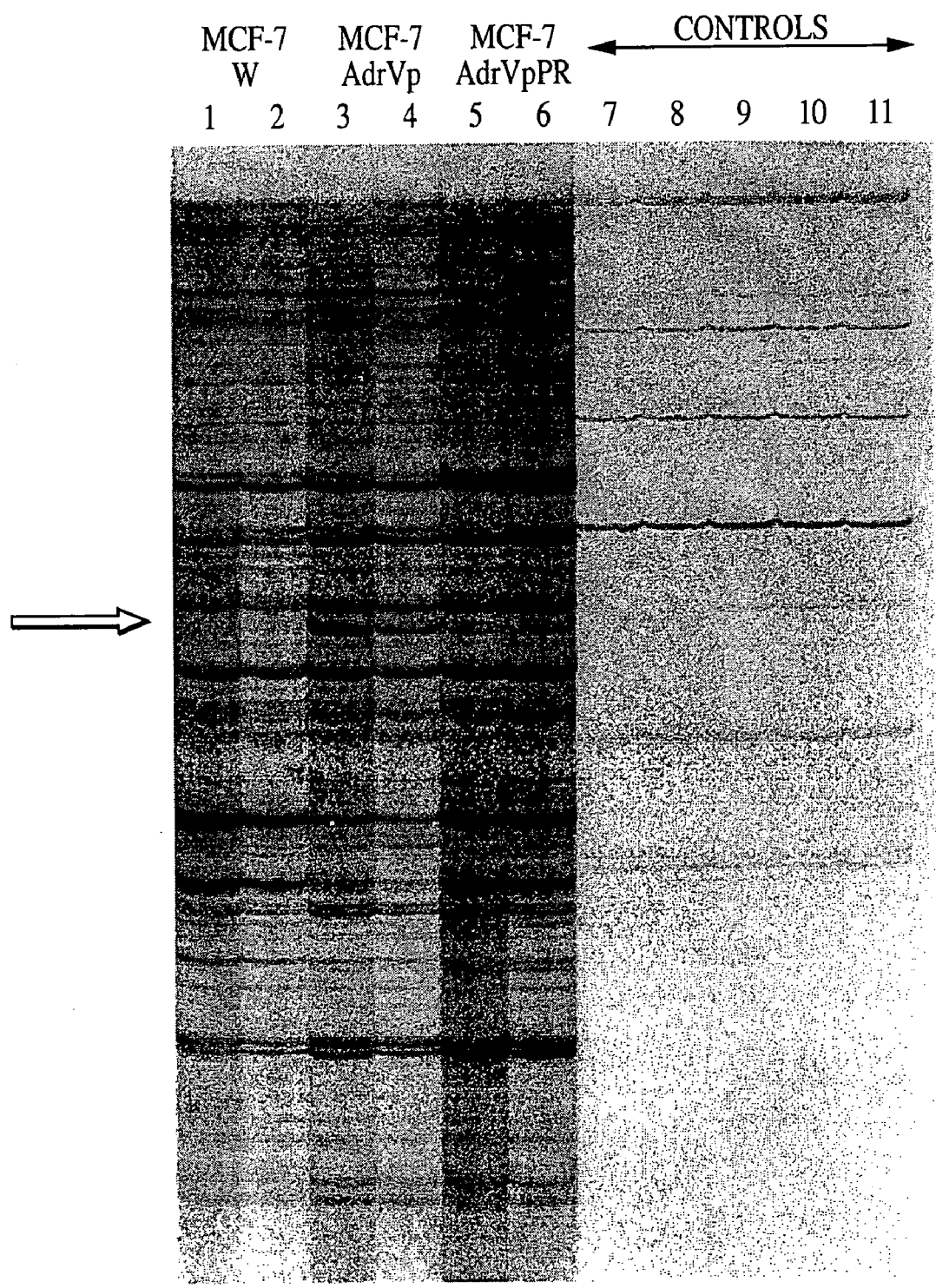
FIG. 1A is an autoradiograph of the RNA fingerprinting of MCF-7 cells.

A novel gene and the protein encoded by said gene, called the Breast Cancer Resistance-associated Protein (BCRP) are described in the instant invention. The BCRP is shown to be overexpressed in human multi-drug resistant (MDR) breast carcinoma cells, colon carcinoma, gastric carcinoma, fibrosarcoma, and myeloma origin. The BCRP is a xenobiotic transporter which confers resistance to multiple chemotherapeutic drugs, and belongs to the ABC transporter superfamily. The BCRP appears to be responsible for the alteration in drug transport and drug resistance manifested by various cancer cells.

The present invention pertains partially to the BCRP, to fragments of this factor, as well as to functional derivatives, agonists and antagonists, and metabolic breakdown products of this factor. The BCRP amino acid sequence is depicted in SEQ ID No. 1 and FIG. 2A. The invention especially concerns agents which are capable of inhibiting BCRP, preferably antibodies to BCRP or antisense probes to the BCRP gene. The invention further encompasses chemical agents which inhibit expression of the BCRP gene or mRNA, including Fumitremorgin C (FTC). The invention also concerns methods of inhibiting activity of BCRP or expression of the BCRP gene by administering such agents.

A "functional derivative" of BCRP is a compound which possesses a biological activity (either functional or structural) that is substantially similar to a biological activity of BCRP. The term "functional derivatives" is intended to include the "fragments," "variants," "analogues," or "chemical derivatives" of a molecule. A "fragment" of a molecule such as BCRP, is meant to refer to any polypeptide subset of the molecule. A functional fragment means that a molecule with a similar, but not identical, amino acid sequence, but has the same function of the full length BCRP. A "variant" of a molecule such as BCRP is meant to refer to a molecule substantially similar in structure and function to either the entire molecule, or to a fragment thereof. A molecule is said to be "substantially similar" to another molecule if both molecules have substantially similar structures or if both molecules possess a similar biological activity.

Thus, provided that two molecules possess a similar activity, they are considered variants as that term is used herein even if the structure of one of the molecules is not found in the other, or if the sequence of amino acid residues is not identical. An "analogue" or agent which mimics the function of a molecule such as BCRP is meant to refer to a molecule substantially similar in function but not in structure to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art. More specifically, the scope of the present invention is intended to include functional derivatives of BCRP which lack one, two, or more amino acid residues, or which contain altered amino acid residues, so long as such derivatives exhibit the capacity to influence cell resistance to chemotherapy.

An "antagonist" of BCRP is a compound which inhibits the function of BCRP. Such antagonists can be immunoglobulins (such as, for example, monoclonal or polyclonal antibody, or active fragments of such antibody). The antagonists of the present invention may also include non-immunoglobulin compounds (such as polypeptides, organic compounds, etc.), and substrates of BCRP transport that may modulate or inhibit the transport of cytotoxic drugs. Antagonists, or inhibitors of BCRP are one embodiment of the invention. These antagonists or inhibitors are useful for inhibiting the drug resistance effect caused by BCRP on cancer cells. The preferred inhibitor is an antibody raised to the BCRP, an antigenic fragment thereof, or a drug which blocks BCRP transporter activity. A preferred inhibitor which is a drug is fumitremorgin C (FTC), a mycotoxin. FTC was obtained from Dr. Lee Greenberg at Wyeth-Ayerst Laboratories in Pearl River, N.Y.

A polyclonal antibody capable of binding to BCRP can be prepared by immunizing a mammal with a preparation of BCRP or functional derivative of BCRP. Methods for accomplishing such immunizations are well known in the art. Monoclonal antibodies or fragments thereof can also be employed to assay for the presence or amount or BCRP in a particular biological sample. Such antibodies can be produced by immunizing splenocytes with activated BCRP (7). The BCRP-binding antibodies of the present invention can be administered to patients to reduce resistance to chemotherapy drugs, and hence enhance their treatment. Methods of administration will depend on the particular circumstances of each individual patient and are within the skill of those skilled in the art.

The BCRP of the present invention may be obtained by natural processes (such as, for example, by inducing the production of BCRP from a human or animal cell); by synthetic methods (such as, for example, by using the Merrifield method for synthesizing polypeptides to synthesize BCRP, functional derivatives of BCRP, or agonists or antagonists of BCRP (either immunoglobulin or non-immunoglobulin); or by the application of recombinant technology (such as, for example, to produce the BCRP of the present invention in diverse hosts, e.g., yeast, bacterial, fungi, cultured mammalian cells, to name a few, or from recombinant plasmids or viral vectors). The compounds of the present invention are said to be "/substantially free of natural contaminants" if preparations which contain them are substantially free of materials with which these products are normally and naturally found.

The choice of which method to employ will depend upon factors such as convenience, desired yield, etc. It is not necessary to employ only one of the above-described methods, processes, or technologies to produce BCRP; the above-described processes, methods, and technologies may be combined in order to obtain BCRP. It is most preferable to prepare BCRP by expressing the gene or cDNA sequence which encodes the BCRP protein. Such gene or cDNA sequence hereinafter termed the "BCRP gene" or "BCRP cDNA sequence".

The technique of RNA fingerprinting was employed to clone the BCRP cDNA. RNA fingerprinting uses the polymerase chain reaction (PCR) and degenerate primer pairs to amplify cellular mRNA. This technique is based on modifications of the technique of "Differential Display of mRNA" developed by Liang and Pardee (6). We used these techniques as a means to discover genes that are differentially expressed in drug-selected cell lines compared to parental cells. The major difference between RNA Fingerprinting and Differential Display is that the mRNA fingerprinting protocol uses a single cDNA synthesis reaction, followed by amplification with upstream and downstream primers. Differential Display uses 9 to 12 cDNA syntheses for each RNA sample with an anchored oligo(dT) primer, followed by amplification with an upstream primer.

The cloned BCRP gene, obtained through the methods described above and in the examples, may be operably linked to an expression vector, and introduced into bacterial, or eukaryotic cells to produce BCRP protein. Techniques for such manipulations are disclosed in Maniatis, T. et al. supra, and are well known in the art (8).

The BCRP cDNA sequence is about 2418 nucleotides long. The BCRP cDNA is depicted in SEQ ID No. 2 or FIG. 2C. The BCRP cDNA can be used to express the BCRP. Also, the BCRP cDNA sequence, or a portion thereof, can be used as a probe in a Northern blot assay or for selection of probes in a RT-PCR assay to measure BCRP mRNA in various tissue samples. Measurement of expression of BCRP by Northern blot or RT-PCR assay can be determinative of drug response to chemotherapeutic drugs over time. The techniques for these assays are described in the examples and are well-known in the art (8). Therefore, such an assay could be used to determine if a patient's failure to respond to chemotherapy is due to overexpression of BCRP, and hence resistance to the drugs. Also, antisense probes could be developed based on the cDNA sequence depicted in SEQ ID 2 and FIG. 2C. These probes can be administered to patients to bind to the BCRP cDNA endogenously and hence inhibit the expression of the BCRP. Such a therapy could be used to halt or slow a patient's propensity to become resistant to the chemotherapy drugs and hence render treatment more effective. Techniques for the production and administration of antisense probes are well known in the art. Techniques of nucleic acid hybridization and cloning are well known in the art (8).

The data presented in the examples and corresponding figures strongly support the conclusion that the novel ABC family member BCRP reported here is a xenobiotic transporter that is primarily responsible for the drug resistance phenotype of MCF-7/AdrVp cells.

The overexpression of BCRP in several cancer cell lines is also shown in the present invention. These cell lines include colon carcinoma cells S1, HT29, gastric carcinoma cells EPG85-257, fibrosarcoma cells EPR86-079, and myeloma 8226 cells. The overexpression of BCRP mRNA in each of these cell lines, and the amplification of the BCRP gene in the drug-resistant cells demonstrate an important role for BCRP in resistance to cytotoxic agents. Furthermore, the enforced overexpression of BCRP in MCF-7 cells diminished daunorubicin cellular accumulation and imparted a pattern of drug cross-resistance to the transfected cells that was virtually identical to that of MCF-7/AdrVp cells. The degree of overexpression of BCRP in transfectant clones 6 and 8 correlates with the alterations in the intracellular steady state level of daunorubicin and their degree of resistance to mitoxantrone, daunorubicin and doxorubicin.

Figure 4A:
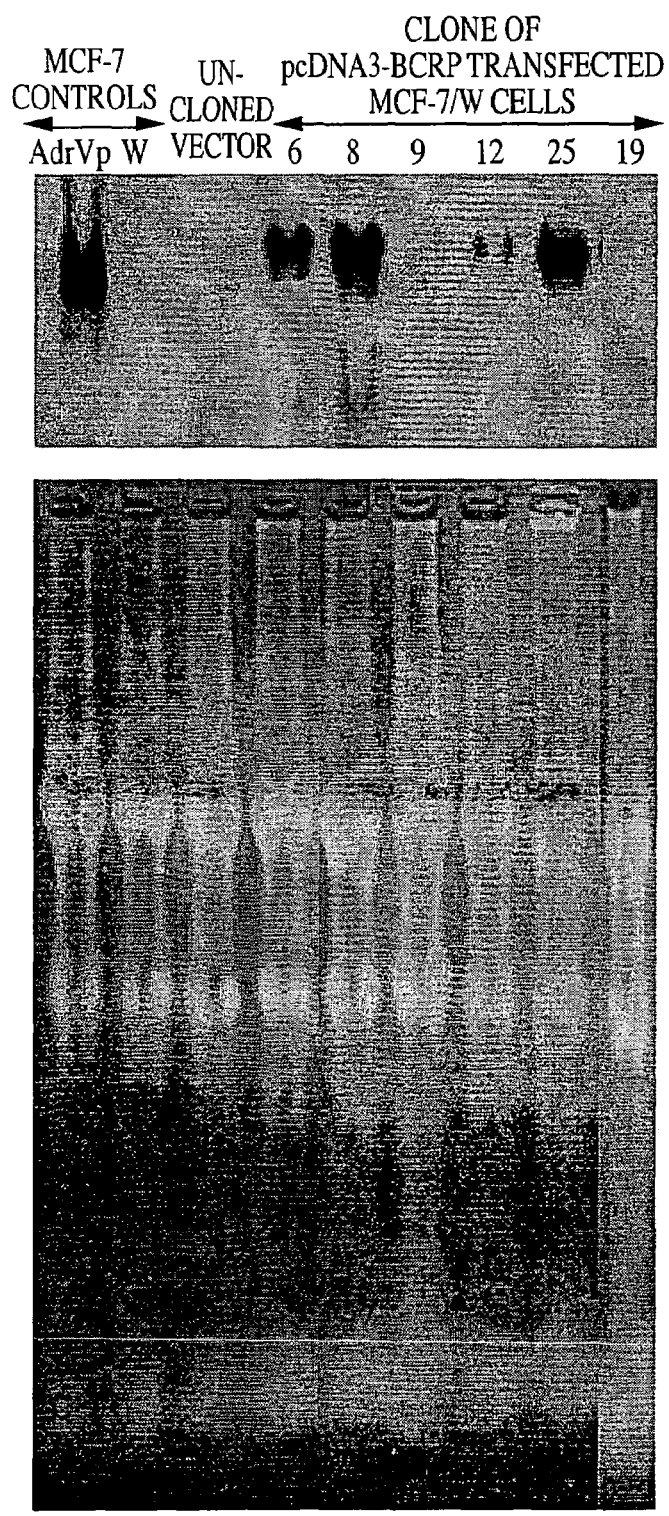
FIG. 4A is an autoradiograph of a Northern blot of subclones of BCRP transfectants demonstrating expression of BCRP mRNA in subclones of MCF-7/W cells stably transfected with the expression vector pcDNA3-BCRP.

A major difference between the BCRP-overexpressing transfectant clones and the original MCF-7/AdrVp subline is that the degree of drug resistance in the latter is greater than in the transfected cells, while the steady state BCRP mRNA levels in each are comparable (FIG. 4A). A number of possibilities may contribute to this difference. Differences in protein stability and/or localization may contribute to the full drug-resistant phenotype, or the expression of other proteins may be required. Recently, we reported that members of the carcinoembryonic antigen (CEA) family, primarily the non-specific cross reacting antigen (NCA) and CEA itself, are markedly overexpressed on the cell surface of MCF-7/AdrVp and MCF-7/AdrVpPR cells compared to drug-sensitive MCF-7 cells (15). A high density of these acidic glycoproteins on the cell surface may protonate drugs such as mitoxantrone, daunorubicin or doxorubicin which prevents entry into the cell. Indeed, Kawaharata, et. al. (16) reported that the enforced expression of CEA in transfected NIH3T3 cells results in both diminished accumulation of and resistance to doxorubicin in the transfected cells. Hence, the relative overexpression of CEA family members on the MCF-7/AdrVp cell surface could act in concert with BCRP to cause greater resistance to mitoxantrone, doxorubicin and daunorubicin than that caused by BCRP alone. This hypothesis could be tested by co-transfecting the MCF-7/BCRP-clone 8 subline with an expression vector containing NCA or CEA.

Another possible explanation for the greater degree of resistance of MCF-7/AdrVp cells compared to the transfectants is that BCRP is part of a multiprotein transporter complex. The translocation pathway of typical ABC transporters consists of two ATP-binding domains and two highly hydrophobic domains which contain membrane-spanning regions. This can be accomplished in a single molecule, as is the case of MRP or Pgp, which are twice the size of BCRP (approximately 1,300 compared to 655 amino acids). Alternatively, the active complex of certain ABC transporters can be formed by the heterodimerization of two non-identical proteins, each of which contains a single ATP-binding and hydrophobic region. The w and brown (b) proteins of *Drosophila* and the Tap-1 and Tap-2 proteins that transport major histocompatibility class I proteins are examples of ABC family members that exhibit such a cooperative interaction. The presence of the phosphopantetheine attachment site on BCRP suggests that BCRP may be a part of a multiprotein complex. Thus, it is possible that BCRP has a protein cofactor(s) which makes it a much more efficient transporter in a heteromeric state. The activation or overexpression of this cofactor in MCF-7/AdrVp relative to MCF-7 cells could explain the increased drug transport in the MCF-7/AdrVp subline relative to the BCRP transfectants.

Figure 10:
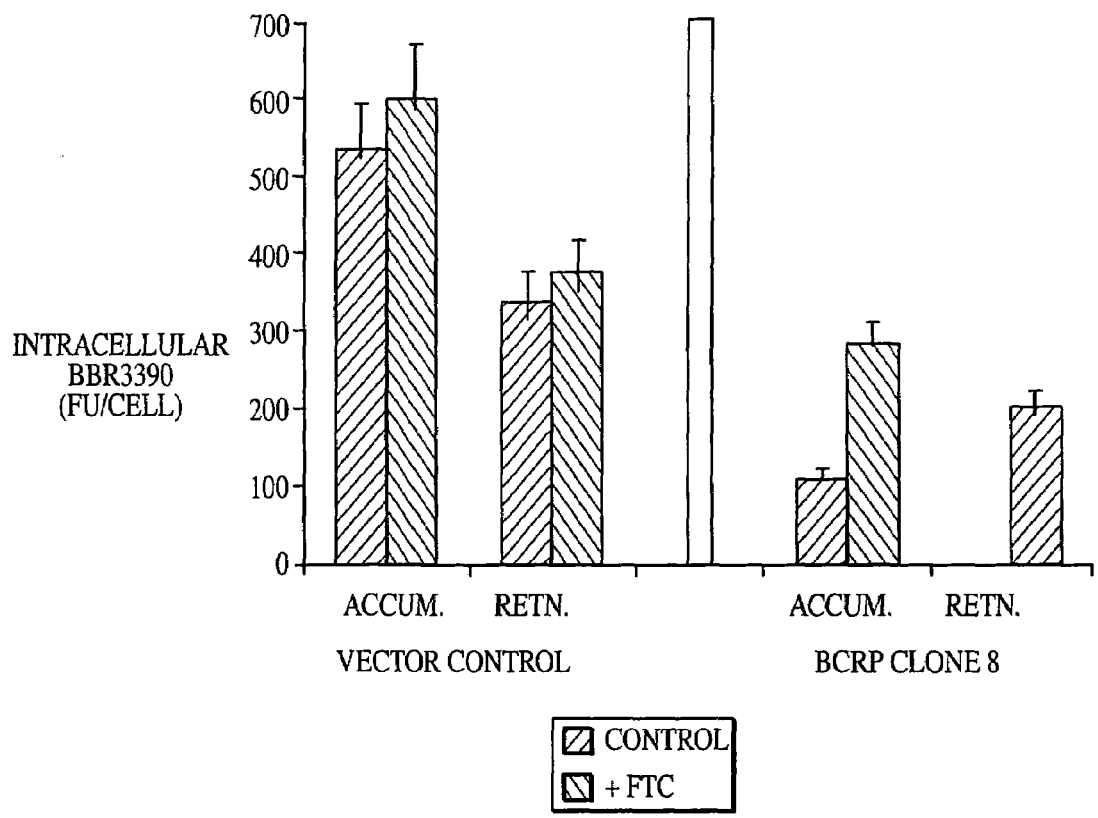
FIG. 10 is a graph showing the results of administration of FTC to BCRP transfected cells.

The finding of elevated expression of BCRP mRNA in the human colon carcinoma S1M1-3.2 cells suggests that BCRP is the "non-Pgp, non-MRP" drug transporter manifested by this multidrug-resistant cell line. This is of particular importance because of the recent report (25) of a specific inhibitor of the transporter identified in S1M1-3.2 cells. This inhibitor, fumitrimorgin C (FTC), does not reverse resistance in cells that overexpress Pgp or MRP. FIG. 10 shows that FTC is able to enhance the accumulation and inhibit the efflux of BBR 3390 (an aza-anthrapyrazole drug that is effluxed by BCRP) in BCRP-transfected MCF-7 cells.

The following examples are provided for illustrative purposes only and are in no way intended to limit the scope of the present invention. All references cited are incorporated by reference.

EXAMPLES

Cell lines. MCF-7 breast carcinoma cells, their drug-resistant subline MCF-7/AdrVp, and a partially drug-sensitive revertant subline (MCF-7/AdrVpPR, obtained from Dr. Antonio Fojo, Medicine Branch, National Cancer Institute), were maintained in culture as described previously (5). The MCF-7/AdrVp subline was continuously maintained in the presence of 100 ng/ml doxorubicin (Pharmacia Adria, Dublin, Ohio) and 5 µg/ml verapamil (Sigma Chemicals, St. Louis, Mo.).

Growth conditions for the cell lines used in the Northern blot studies are contained in the references listed in Table 1. The S1M1-3.2 colon carcinoma cells were derived from S1 cells (a subclone of human colon carcinoma cell line LS174T) by selection for growth in increasing concentrations of mitoxantrone until a final concentration of 3.2 µM was acheived. HL-60/MX2 cells were purchased from the American Type Culture Collection (Manassas, Va.), and maintained in culture as described previously (17).

Example 1

Synthesis of cDNA by Reverse Transcription of mRNA

Purified total cellular RNA (2 µg) from MCF-7/W, MCF-7/AdrVp or MCF-7/AdrVpPR cells which have partially reverted to drug sensitivity by culture in the absence of the selecting agents were reverse transcribed with 200 units of Moloney murine leukemia virus reverse transcriptase in the presence of an oligo(dT) primer (0.1 µM), and 1 mM dNTP at 42° C. for 1 hour. The reactions were terminated by heating at 75° C. for 10 minutes. The cDNAs thus produced were stored at −20° C. until further use.

Example 2

RNA Fingerprinting

RNA fingerprinting was performed using the Delta™ RNA fingerprinting kit (Clontech Laboratories, Palo Alto, Calif.), with minor modifications. RNA fingerprinting is accomplished by amplification of the cDNA by the polymerase chain reaction (PCR), using random primers.

For each fingerprinting reaction, cDNA diluted 1:10 (dilution A) or 1:40 (dilution B) from each cell line was amplified with one upstream (P) and one downstream (T) primer in the presence of 50 µM dNTP, 50 nM [$^{33}$P]dATP, and the "Advantage KlenTaq Polymerase Mix" supplied with the Clontech kit. The upstream P primers were arbitrary 25-mers. The downstream T primers were 30-mer anchored oligo(dT)primers whose 3' terminal contained the sequence 5'-$T_9N_1N_1$-3', where $N_1$ is A, C or G. The P primer binds to the cDNA based on chance homology. We paired ten P primers and nine T primers to give 90 possible combinations.

The first three PCR cycles were performed at a relatively low stringency (annealing temperature 40° C.). Because of this, the P primer bound imperfectly, which increased the number of amplified products. The products of these early cycles were then amplified by 24 PCR cycles at high stringency (annealing temperature 60° C.). Control PCR reactions were prepared containing sterile water instead of cDNA (water control), or 0.02 µg of total cellular RNA (RNA control). The RNA controls were prepared to assess whether the RNA was contaminated with genomic DNA.

Following the PCR reaction, a small amount of each reaction mixture was loaded onto a 5% polyacrylamide gel, after which the gels were dried, then autoradiographs made (FIG. 1A). These autoradiographs demonstrated a characteristic "RNA Fingerprint" pattern of 50 to 100 PCR product bands of 100 to 2000 nucleotides in length. Lanes 1, 3, and 5 are reaction mixes where cDNA diluted 1:10 (dilution A) was added; lanes 2, 4, and 6 represent reaction mixtures where cDNA diluted 1:40 (dilution B) was added. Lanes 7 and 8 are "H$_2$O controls", where sterile water was added to the PCR reaction mixture instead of cDNA. Lanes 9, 10 and 11 are "RNA controls", where 0.02 µg of cellular RNA from MCF-7/W, MCF-7/AdrVp, or MCF-7/AdrVpPR cellular is added instead of cDNA. These "RNA controls" serve to indicate contamination of the RNA with genomic DNA. The autoradiographs were inspected for PCR products that were produced in greater abundance in reactions that used reverse transcribed RNA from MCF-7/AdrVp cells, compared to those that used RNA from MCF-7/W or MCF-7/AdrVpPR cells (FIG. 1A). The ARROW indicates a PCR product that represents a mRNA species that is overexpressed in MCF-7/AdrVp cells, compared to MCF-7/W or MCF-7/AdrVpPR cells. This is the PCR product that was cut out of the gel and amplified and cloned using the "TA Cloning" method, the desired clone of which was called Clone 8 (see below).

Example 3

Amplification of the Target cDNA by TA Cloning

The PCR product overexpressed in MCF-7/AdrVp cells was excised from the dried gel and eluted by boiling in 40 ml ddH$_2$O for 5 min, then amplified by PCR for 20 cycles using the original primers and separated on 2% agarose/ethidium bromide gels. These PCR products were then ligated into a "TA Cloning Vector" plasmid, pCR®2.1, which was then cloned using standard techniques for PCR products (Original TA Cloning® Kit, Invitrogen Corporation, San Diego, Calif.).

The pCR®2.1 plasmids containing the PCR product were used to transform the TOP 10F strain of *E. coli*. Individual bacterial colonies were picked and plasmid DNA was isolated by minipreps (WIZARD™ Miniprep, Promega, Madison, Wis.). Plasmid DNA was amplified by PCR with the original "P" and "T" primers, then subjected to gel electrophoresis. The original sized band was cut out, and the DNA was isolated by boiling in 100 µl ddH$_2$O at 100° C. for 5 min. An aliquot of the DNA was reamplified by PCR with the original primers for 20 cycles. A single band was visualized on ethidium bromide gels which was cut out, electroeluted then precipitated.

Example 4

Isolation of the BCRP Clone

Figure 1B:
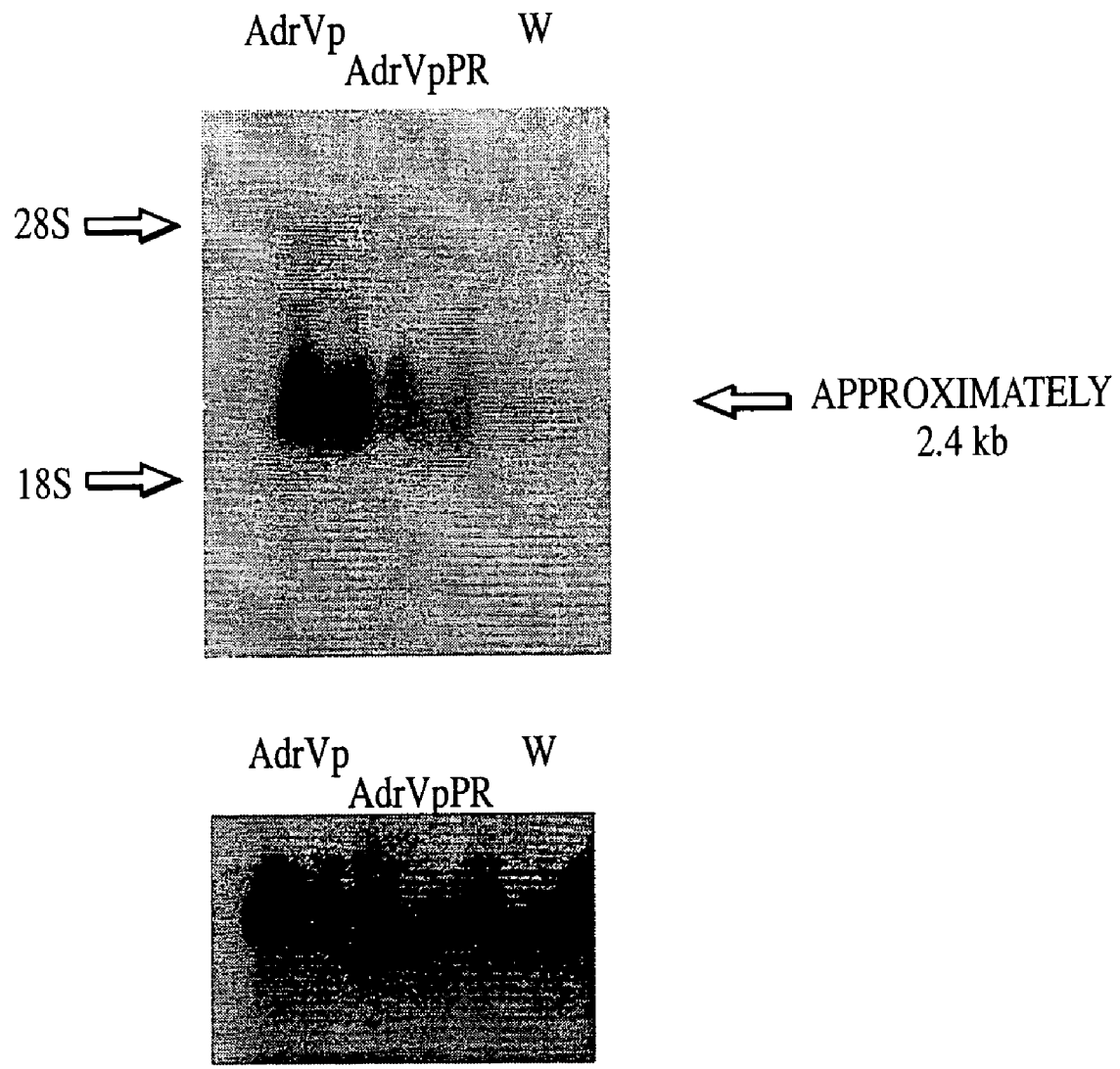
FIG. 1B is an autoradiograph of a Northern blot hybridization of mRNA from MCF-7/W (W), MCF-7/AdrVp AdrVp), and MCF-7/AdrVpPR (AdrVpPR) cells.

The "reverse" Northern blot method was used to screen the TA vector clones. Briefly, a "reverse" Northern analysis was performed as follows. The PCR product isolated from 12 different colonies of *E. coli* that was transformed by the pCR2.1 plasmid were fixed in duplicate to ZETA PROBE™ membranes (BioRad, Richmond, Calif.) in a slot blot apparatus. One of the duplicate membranes was probed with the [$^{33}$P]-labeled PCR reaction mixture that amplified MCF-7 cDNA using the original "P" and "T" primers in the RNA Fingerprinting kit. The other membrane was probed with the original [$^{33}$P]-labeled parallel PCR reaction mixture that amplified the cDNA produced from MCF-7/AdrVp cells, using standard Northern blot conditions of hybridization, after which the binding of probe was assessed by autoradiography. A single TA clone (Clone 8-SEQ ID No. 7) was thus identified whose PCR product insert identified a 2.4 kb mRNA species that was markedly overexpressed in MCF-7/AdrVp cells, compared to MCF-7 cells (FIG. 1B, top panel). The partially revertant MCF-7/AdrVpPR subline had intermediate expression of the 2.4 kb mRNA species (FIG. 1B, top panel). To control for equivalence in lane loading, the blot was stripped then reprobed with radiolabeled 18S RNA (FIG. 1B, bottom panel).

Figure 1C:
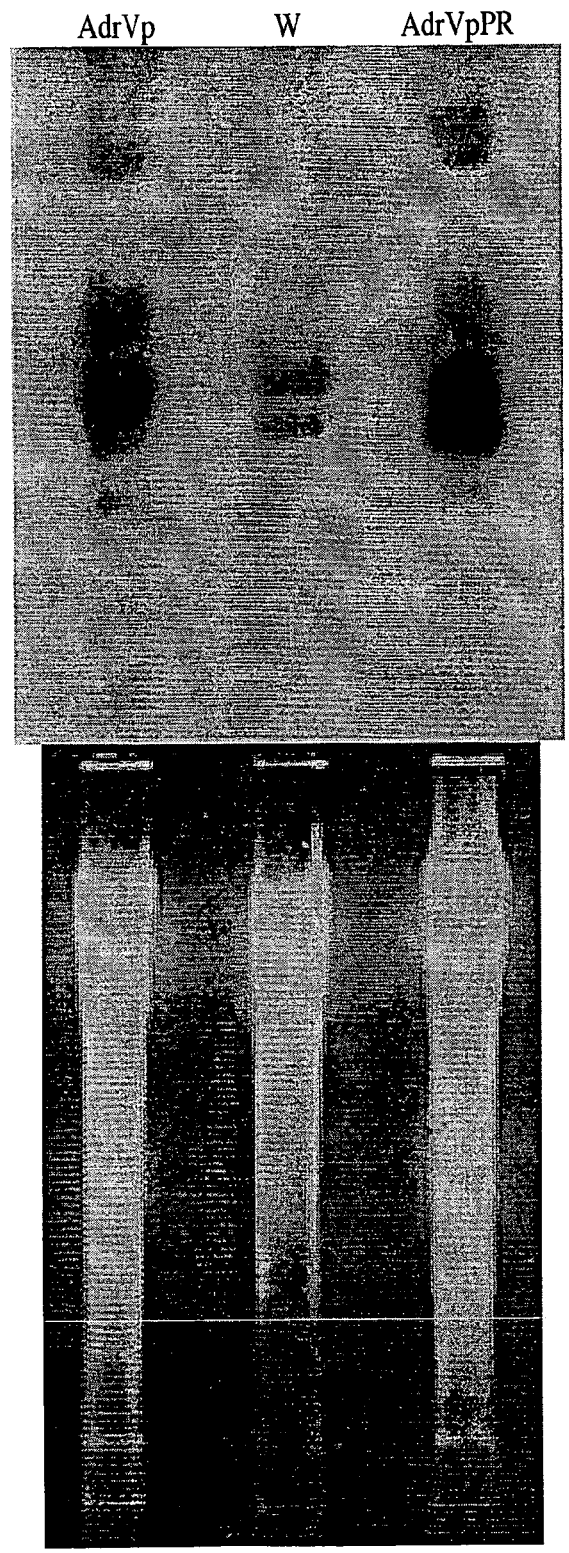
FIG. 1C is an autoradiograph of a genomic Southern blot hybridization of DNA from MCF-7/AdrVp (AdrVp), MCF-7/W (W) and MCF-7/AdrVpPR (AdrVpPR) cells.

Southern blots were performed using the Clone-8 PCR product. Briefly, DNA was isolated, digested with EcoR1, subjected to agarose gel electrophoresis, transferred and fixed to a nitrocellulose filter. The filter was probed with the Clone-8 PCR product that was end-labeled with [$^{32}$P]-dCTP, then the radioautograph shown was made (FIG. 1C, top panel). This demonstrated that the cognate gene for BCRP was amplified in both MCF-7/AdrVp and MCF-7/AdrVpPR cells, compared to parental MCF-7 cells (FIG. 1C, top panel). The lower panel in FIG. 1C shows the ethidium bromide-stained agarose gel electrophoretogram of the corresponding genomic DNA after digestion with EcoR1, to demonstrate approximate equivalence of gel loading.

Example 5

Sequencing of the BCRP Clone

Sequencing of the cDNAs was performed with an automated DNA sequencer (Perkin Elmer, Inc., Foster City, Calif.). All DNA sequences were confirmed by sequencing in the reverse direction. The differentially expressed PCR product in the TA Clone 8 was sequenced and found to be a 795 bp cDNA (SEQ ID No. 7). Protein database searches of the deduced amino acid sequence revealed a high degree of homology to members of the ABC superfamily of transporter proteins.

Example 6

Isolation of the Full-length BCRP cDNA

An MCF-7/AdrVp cDNA library was constructed using the CAPFINDER™ PCR cDNA library construction kit (Clontech) according to the manufacturer's protocol. The CAPFINDER™ technique is designed specifically to produce full-length double stranded cDNA. The 795 bp Clone 8 cDNA fragment was radiolabeled and used as a probe to screen the cDNA library prepared from MCF-7/AdrVp cells. Positive clones isolated were subjected to secondary and tertiary screening, then tested by Northern blot hybridization using RNA obtained from MCF-7, MCF-7/AdrVp and MCF-7/AdrVpPR cells. Multiple clones were found to have 2.4 kb inserts, the approximate size of the BCRP mRNA suggested by Northern blotting.

Four of the 2.4 kb inserts were ligated into the pCR2.1 plasmid, then these TA vectors were cloned in *E. coli* (as described above). One TA vector done containing a 2.4 kb cDNA fragment insert was identified and isolated. Sequencing of the 2.4 kb cDNA insert was performed with an automated DNA sequencer (Perkin Elmer Inc., Foster City, Calif.). All DNA sequences were confirmed by sequencing in the reverse direction. After sequencing, the cDNA insert was found to be 2418 bp in length as in FIG. 2C or SEQ ID No. 2. Analysis of the cDNA for open reading frames (ORF) using the program "FRAMES" contained in the Genetics Computer Group (GCG) software package indicated the presence of a long ORF that began at position 239, and ended with the stop codon TAA at position 2204-6. The deduced amino acid sequence of this ORF is shown in FIG. 2A, and SEQ ID No. 1. The protein has 655 amino acids and a approximate molecular weight of about 72.3 kilodaltons. The protein encoded by this sequence has been designated Breast Cancer Resistance Protein, or BCRP (FIG. 2A).

Analysis of the sequence of BCRP with the GCG program "MOTIFS" demonstrated a single Walker "A" ATP/GTP binding region (11) at amino acids 80-87 and a phosphopantetheine attachment site at amino acids 213-228 (FIG. 2A). Phosphopantetheine (or pantetheine 4' phosphate) is the prosthetic group of acyl carrier proteins in some multienzyme complexes where it serves in the attachment of activated fatty acid and amino-acid groups (12).

Figure 2B:
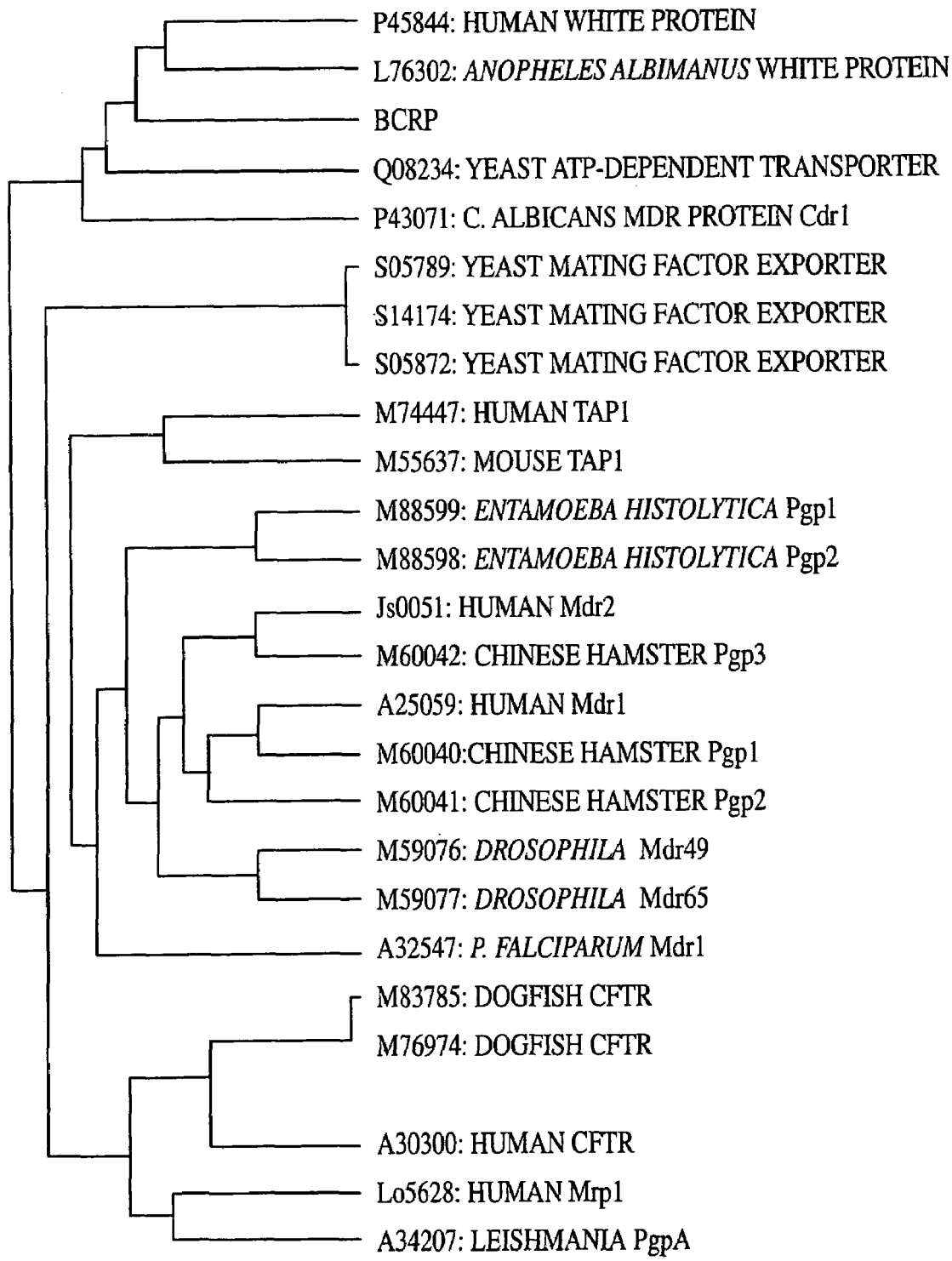
FIG. 2B shows the relative similarity of BCRP to selected members of the ABC transporter superfamily.
Figure 2D:
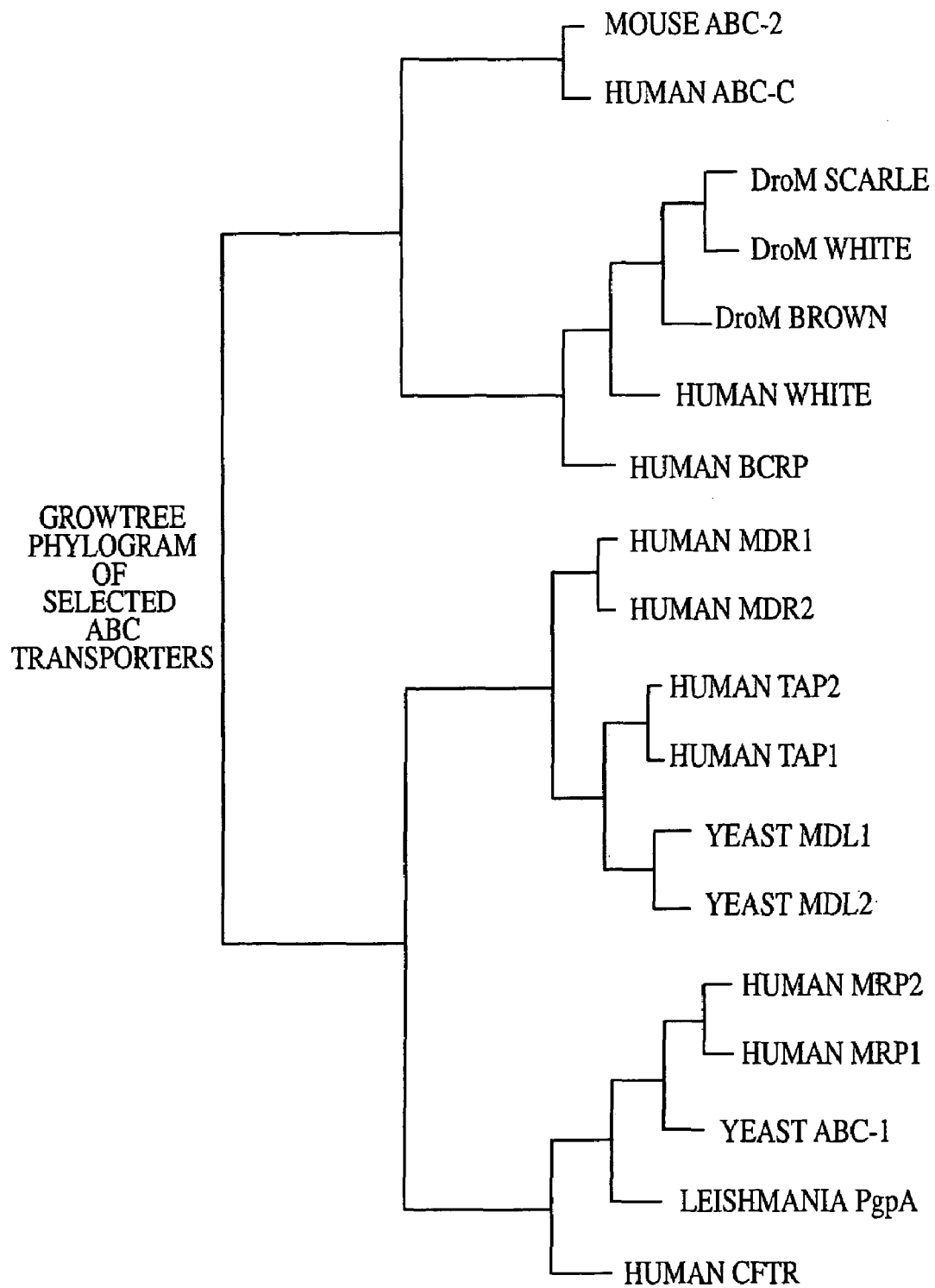
FIG. 2D is a graph of a phylogram showing the evolution of the amino acid sequence of BCRP in relation to certain other members of the ABC family of transport proteins.

Examination of BCRP structure with GCG programs "PEPPLOT" and "PLOTSTRUCTURE" revealed a relatively hydrophilic amino-terminal domain (amino acids 1-400) that contains the ATP-binding sequence and a relatively hydrophobic carboxy-terminal domain (amino acids 401-655), containing at least three putative transmembrane domains (TM1, TM2, and TM3), and four potential N-glycosylation sites (Glyc) (FIG. 2A). The transmembrane domains were estimated by the use of a program to predict helices in integral membrane proteins (13). Analysis of the BCRP sequence by the GCG program "DOTPLOT" demonstrates that the peptide is homologous with one-half of the duplicated Pgp or MRP molecule, except that Pgp or MRP have the configuration $NH_2$-[transmembrane domains]-[ATP binding 1]-[transmembrane domains]-[ATP binding 2]-COOH, whereas that of BCRP is $NH_2$-[ATP binding]-[transmembrane domains]-COOH. The relative similarity of BCRP to other members of the ABC transporter superfamily was determined using the "PILEUP" program of GCG. This analysis demonstrated that the peptide sequence of BCRP is only distantly related to P-glycoprotein (PgP or Mdr1) or MRP (FIG. 2B).

Example 7

Comparison of BCRP Sequence to the w Sequence

Analyses of cDNA and deduced protein sequences were accomplished using protein and nucleotide sequence databases that were accessed using the Wisconsin Sequence Analysis Package Version 8 (Genetics Computer Group [GCG], Madison, Wis.) which are available through the Frederick Cancer Research Center's Supercomputing Facility (Frederick, Md.).

Figure 4B:
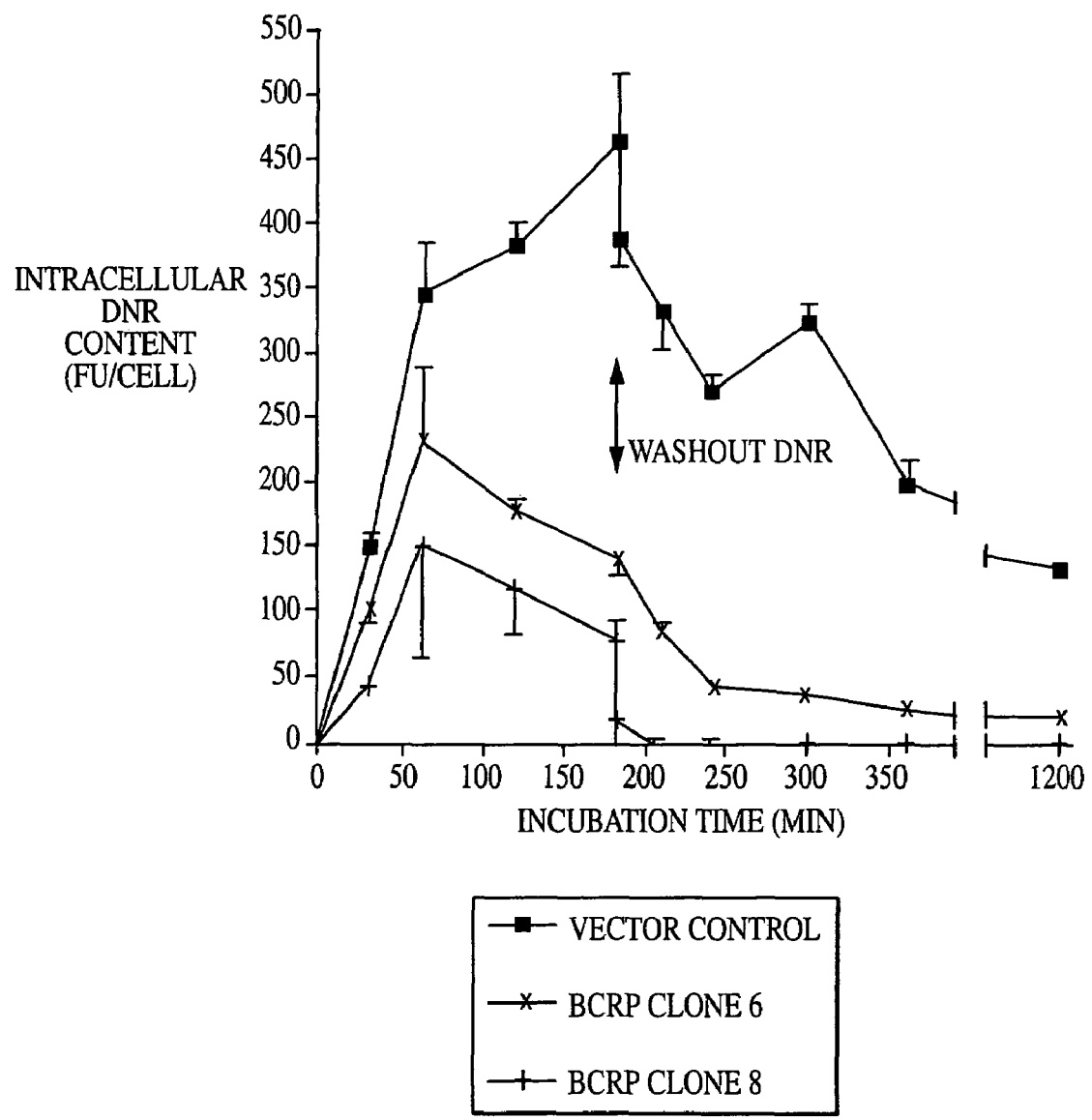
FIG. 4B is a graph of Daunorubicin (DNR) accumulation and retention in the pcDNA3 vector control cells and BCRP-transfected clones 6 and 8.
Figure 4C:
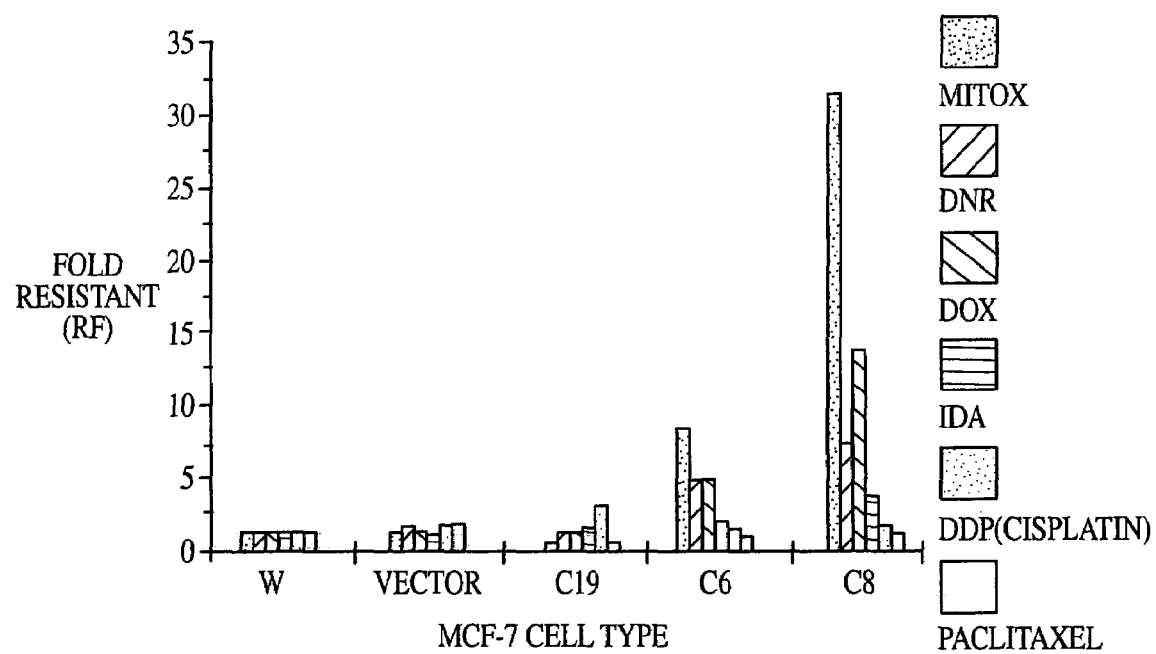
FIG. 4C shows the relative resistance factors-MCF-7, vector control, clones 19, 6, and 8.
Figures 1, 4D:
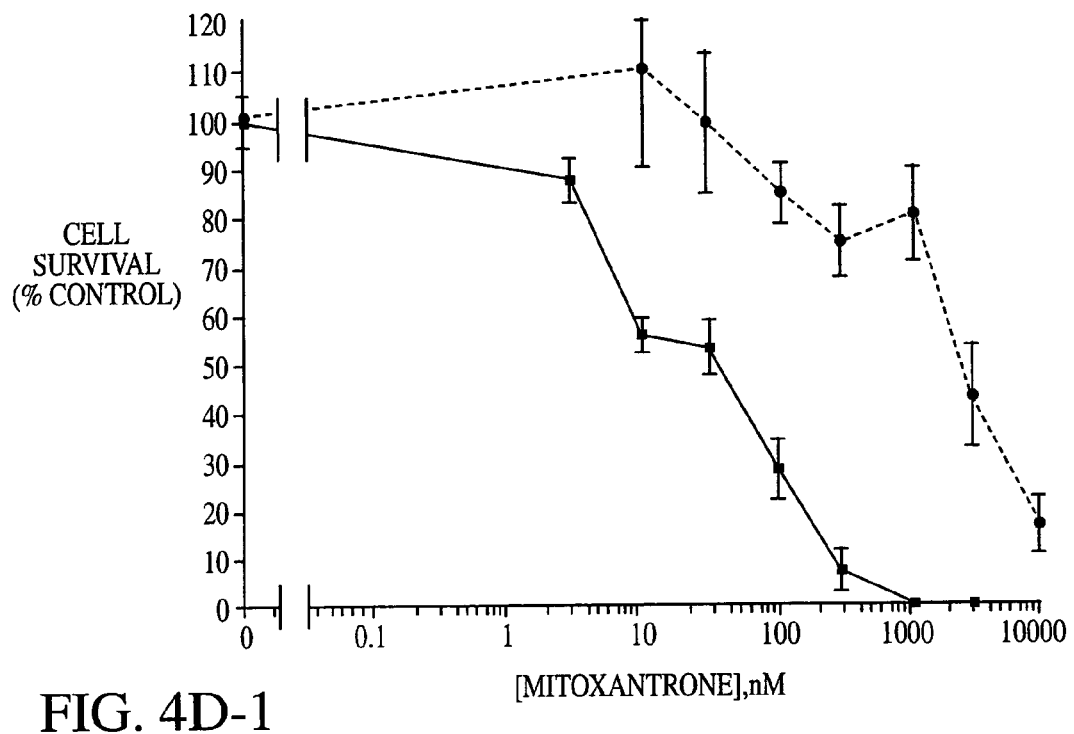
Figures 2, 4D:
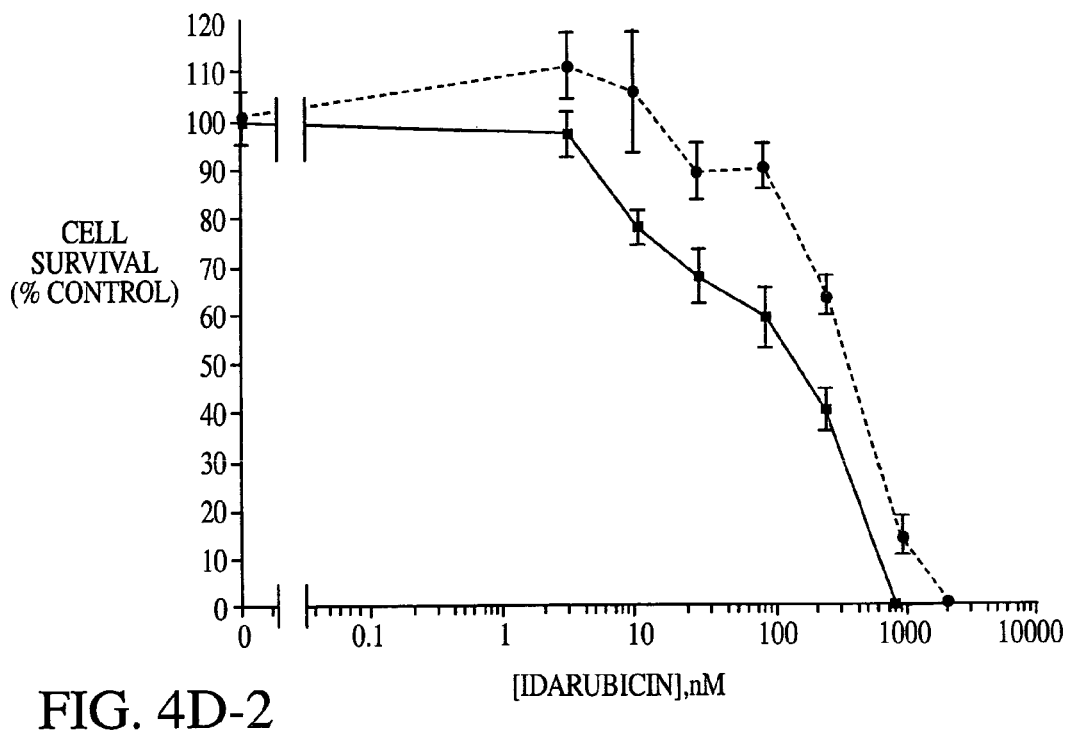
Figures 3, 4D:
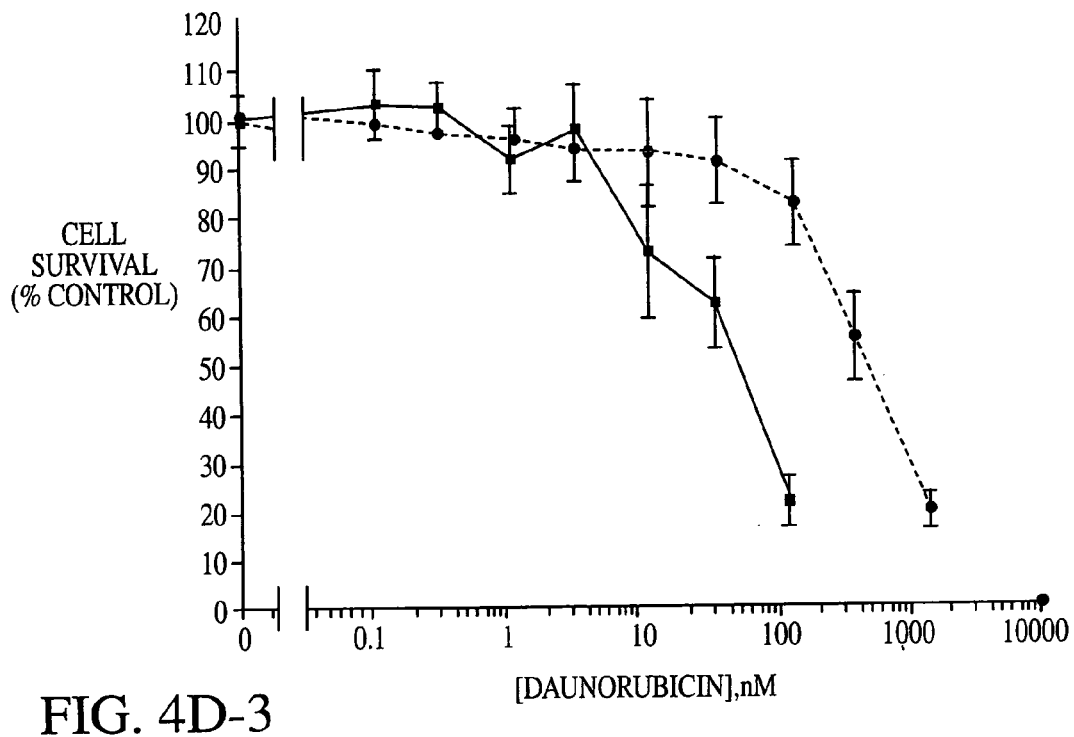
Figures 4, 4D:
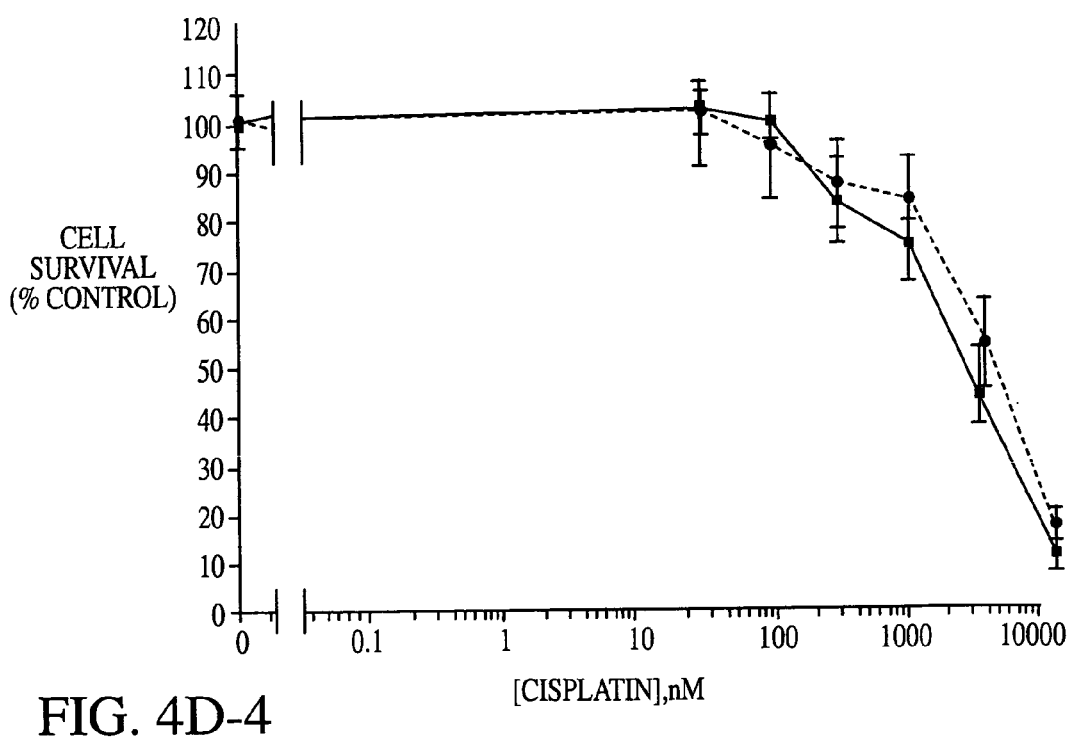
Figures 4, 4D, 5:
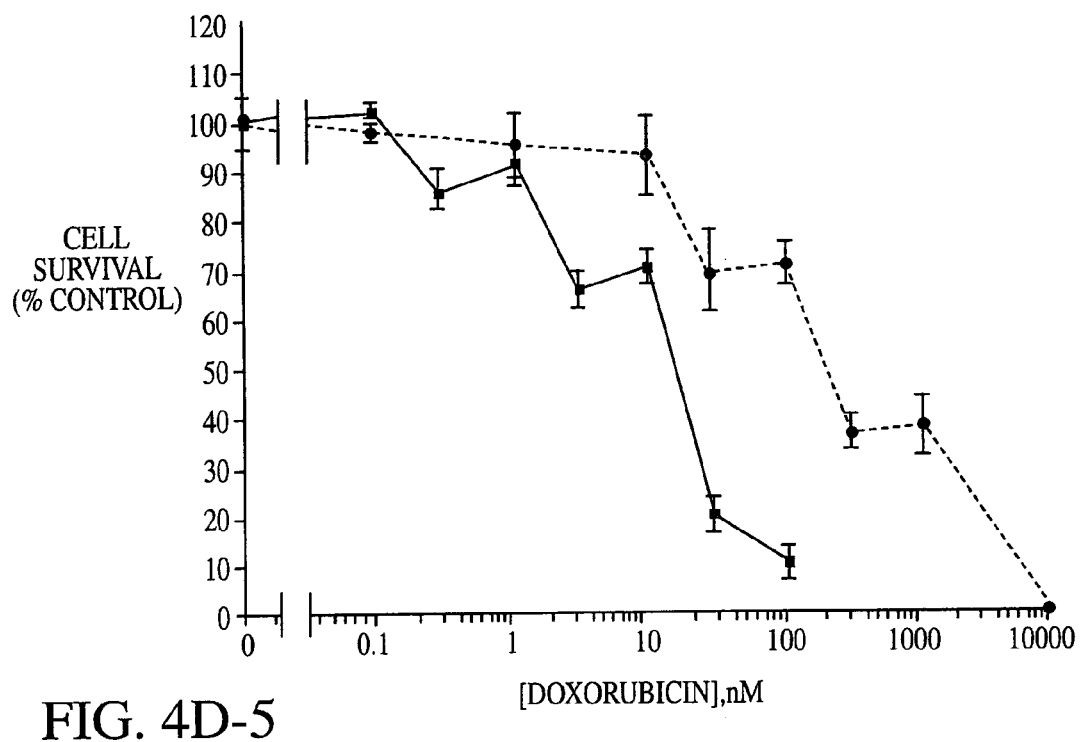
Figures 4, 4D, 5, 6:
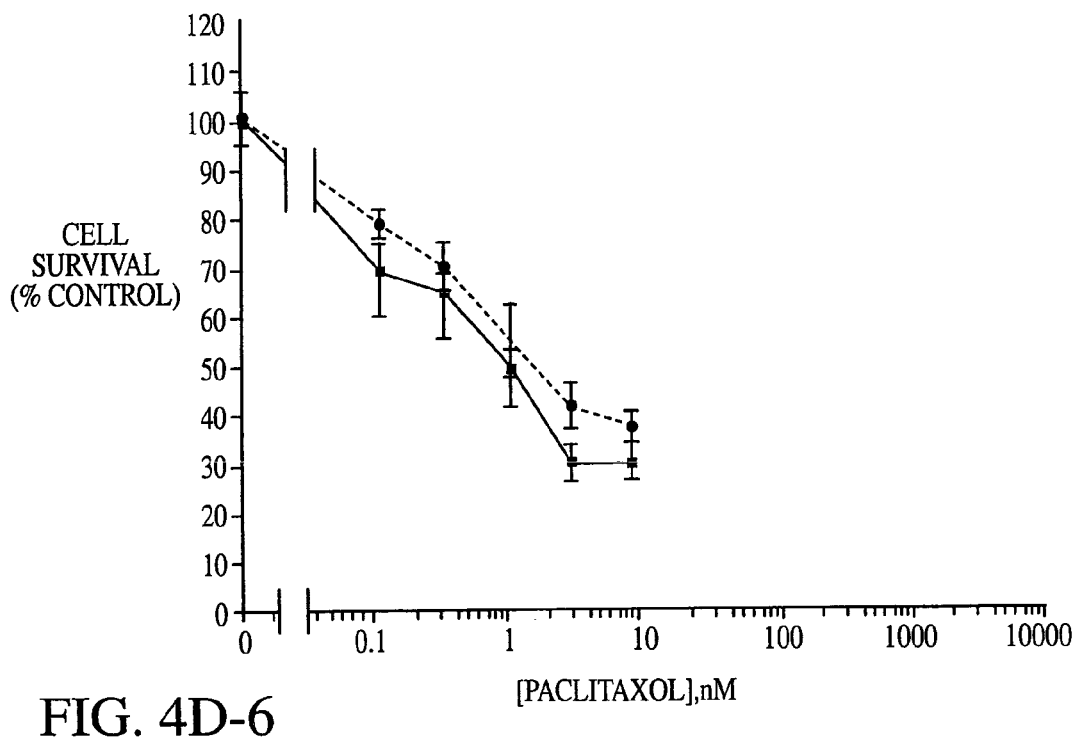
Figure 4E:
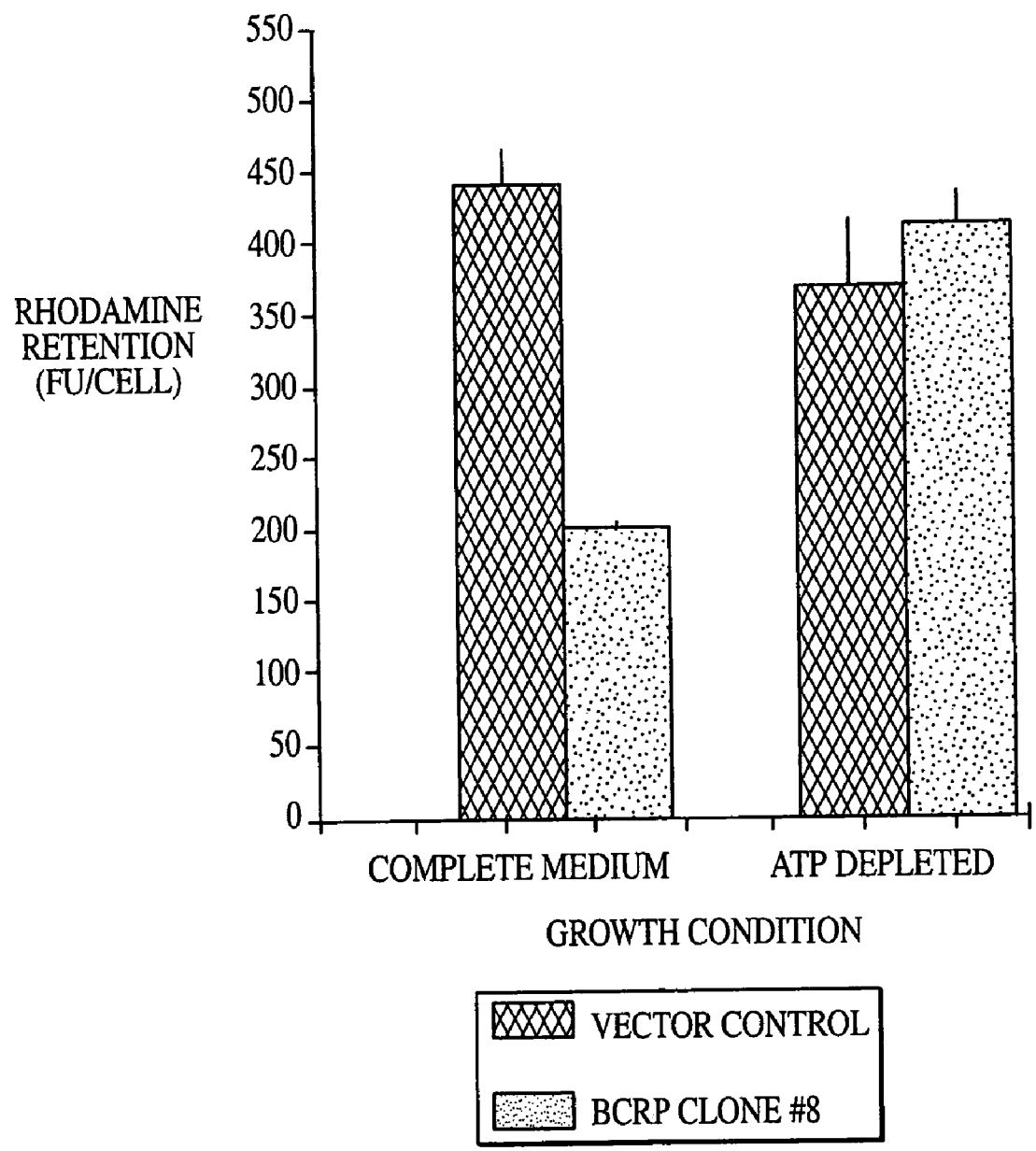
FIG. 4E shows a graph of the effects of ATP deletion of the retention of rhodamine 123 by transfectant MCF-7/pcDNA3 (empty vector control) or MCF-7/BCRP clone 8 cells.
Figure 6:
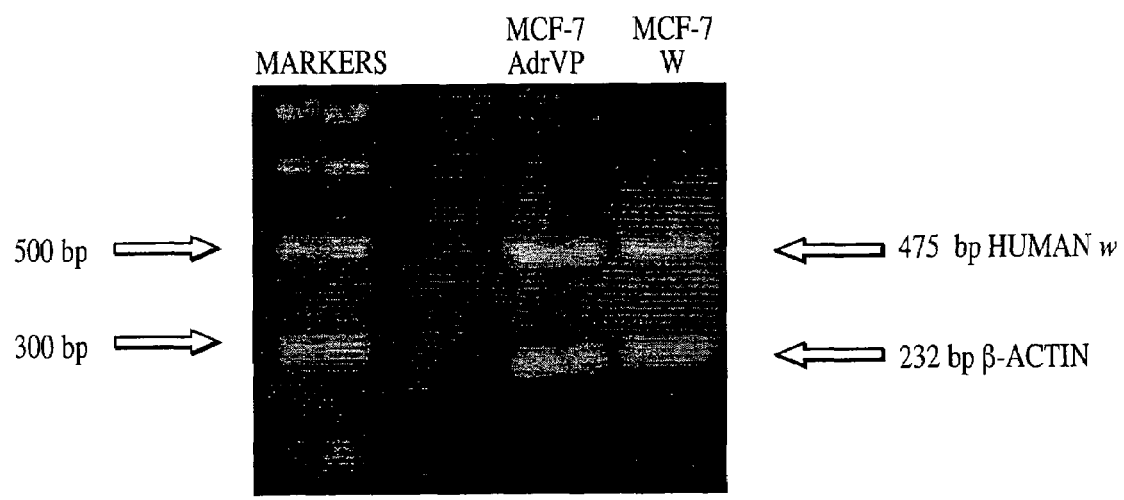

A "FASTA" comparison of the BCRP amino acid sequence revealed a high degree of homology to at least 50 ATP-binding cassette transport proteins. The highest match was PIR2: G02068, the human homologue of the *Drosophila* white (w) gene, which has 638 amino acids, and is 29.3% identical to BCRP. The w gene in *Drosophila* functions in the cellular transport of guanine and tryptophan, which are retinal pigment precursors (9). We found that the human homologue of w is not overexpressed in MCF-7/AdrVp cells compared to MCF-7 cells, as detected by a reverse-transcription PCR assay (FIG. 6).

The program "Oligo" (Version 5.0, National Biosciences, Inc., Plymouth, Minn.) was used to help determine suitable primers for detection of the human homologue of w by reverse transcription-PCR. These assays were done using a modification of those described previously for beta actin and MRP (10), except that primers specific for the w gene were used instead of MRP. The upper primer began at 5' position 2136 of human w mRNA, and had the sequence 5'-CGA CCG ACG ACA CAG A-3') (SEQ ID No. 3); The lower primer began at 3' position 2590, and had the sequence 5'-CTT AAA ATG AAT GCG ATT GAT-3') (SEQ ID No. 4). To assure uniformity of gel loading, a reverse transcription-PCR assay for beta-actin was also performed. The final concentrations of primers used was 200 nM. Twenty-five cycles of denaturation (94° C., 1 minute), annealing (50° C., 1 minute) and elongation (72° C., 2 minutes) were carried out. FIG. 6 shows an agarose gel electrophoresis of an aliquot of the PCR reaction mixtures that used RNA from MCF-7 or MCF-7/AdrVp cells demonstrating that both human w and beta-actin are expressed approximately-equally in these cell lines.

Example 8

Northern Blots of Various Human Tissue with BCRP Probe (Clone 8)

Figure 3:
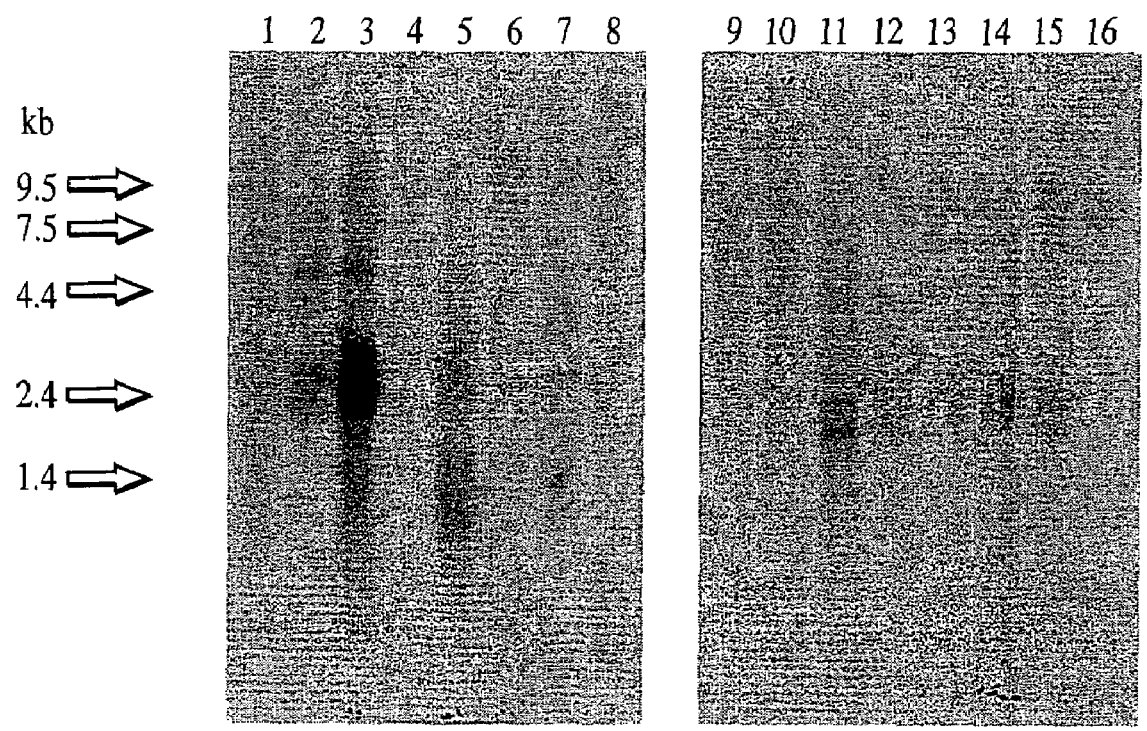

Northern blotting with a $^{32}$P-labeled Clone 8 cDNA probe was performed. Pre-blotted agarose gel-electrophoresed RNA from multiple tissues was purchased from Clontech, for use in multiple tissue Northern blot assays (FIG. 3). The greatest expression of BCRP was seen in placental tissue, with lower amounts of expression demonstrable in brain, prostate, small intestine, testis, ovary, colon and liver. BCRP transcripts were below the level of detection in heart, lung, skeletal muscle, kidney, pancreas, spleen, thymus and peripheral blood leukocytes.

Example 9

Expression of BCRP in MCF-7 Cells—Functional Studies

The full-length BCRP cDNA was inserted into the multiple cloning site of expression vector pcDNA3 (Invitrogen). Following subcloning of the pcDNA3-BCRP construct, DNA sequence analysis was performed to confirm that the insert in the clone that was chosen was in a sense orientation to the CMV promoter of the pcDNA3 vector. MCF-7 cells were transfected with pcDNA3-BCRP, using the calcium phosphate precipitation method (17), selected by culture with geneticin (G418, 1 mg/ml), then subcloned by limiting dilution in 96 well flat-bottomed culture plates. Subclones were tested for expression of BCRP mRNA by Northern blot analysis, using radiolabeled Clone 8 cDNA as a probe (FIG. 4A). As a control, MCF-7 cells were also transfected with the empty pcDNA3 vector, then selected by growth in medium containing 1 mg/ml G418 (FIG. 4A). Two clones of MCF-7 cells transfected with pcDNA3-BCRP that were found to overexpress BCRP (clones 6 and 8) were selected and expanded for further studies (FIG. 4A). A third clone of pcDNA3BCRP transfected cells, clone 19, did not overexpress BCRP, and was selected for study as a control.

Example 10

Effect of Chemotherapeutic Drugs on BCRP-Transfected MCF-7 Cells

Daunorubicin accumulation and retention was examined in the transfected cells by means of flow cytometry. The BCRP-overexpressing clones 6 and 8 displayed diminished accumulation and retention of daunorubicin, compared to the vector-transfected controls (FIG. 4B), with intracellular steady-state concentrations of drug in clones 8 and 6 respectively approximately 30% or 50% of that attained in the vector control cells. This difference was not due to differences in cell volume, since the volumes of the BCRP-overexpressing sublines tested was not less than that of the empty vector-transfected control cells. The cell volumes, measured by COUTLTER CHANNELYZER™ are 2515±56, 3074±112 and 2459±56 $um^3$ for MCF-7/BCRP-clone 6, MCF-7/BCRP-clone 8 and MCF-7/pcDNA3 vector control cells, respectively. These values are comparable to our previous measurements of MCF-7 cell volumes (5).

The sensitivities of the various transfected sublines to chemotherapeutic agents were tested by the sulforhodamine-B (SRB) cytotoxicity assay (14). The $LC_{50}$, defined as the concentration of drug that caused lethality to 50% of the cells, was calculated. From this, the "Fold of Resistance" (RF) was calculated by dividing the $LC_{50}$ for a given drug against a transfected cell line by the $LC_{50}$ of that drug against non-transfected MCF-7 cells. The BCRP-overexpressing clones 6 and 8 displayed resistance to mitoxantrone, daunorubicin and doxorubicin, compared to non-BCRP-overexpressing clone 19 cells, MCF-7 cells, or the empty vector-transfected controls (FIGS. 4C, 4D, 5). FIG. 5 contains the median $LC_{50}$ values for multiple cytotoxicity experiments for all cell lines and drugs tested. FIG. 4D shows typical $LC_{50}$ studies for the six drugs tested for MCF-7/W and MCF-7/pcDNA3-BCRP clone8 cells to illustrate the data from which the $LC_{50}$ values were derived, and the accuracy of the measurements. The asterisk and solid line in FIG. 4D indicate MCF-7/W cells, the closed squares and dotted lines represent MCF-7/pcDNA3-BCRP clone 8 cells. The vertical bars in the figure represent the standard deviation of six replicate determinations.

Like MCF-7/AdrVp cells, the MCF-7/BCRP transfectant clones 6 and 8 displayed the greatest degree of resistance to mitoxantrone. The pattern of cross-resistance displayed by the BCRP-overexpressing transfected cells is very similar to that displayed by MCF-7/AdrVp cells, except that MCF-7/AdrVp cells have greater relative resistance to all cytotoxic drugs within the phenotype. The BCRP-transfected clones 6 and 8 remained relatively sensitive to idarubicin, cisplatin and paclitaxel (taxol), as are MCF-7/AdrVp cells (FIGS. 4C, 4D and 5).

To determine the effects of ATP depletion on the retention of rhodamine 123 by the BCRP transfected cells compared to controls, cells were incubated in complete medium or under ATP-depleting conditions. MCF-7 cells were depleted of ATP by incubation in glucose-free DMEM containing 50 mM 2-deoxy-D glucose and 15 mM sodium azide for 20 minutes (37° C.). Rhodamine 123 was added (0.5 µg/ml final concentration) for an additional 30 minutes. The cells were placed on ice, washed free of rhodamine, and incubated under ATP-depleting conditions for an additional 30 minutes, and rhodamine retention was determined by flow cytometry (excitation 488 nm, emission 520 nm). This demonstrates that the transport function of BCRP appears to depend on ATP.

Example 11

Expression of BCRP in Blast Cells from Patients with Acute Myelogenous Leukemia (AML) as Detected by a Reverse-transcription Polymerase Chain Reaction (RT-PCR) Assay The RT-PCR assays were performed using a modification of those described previously for beta actin and MRP (10), except that primers specific for BCRP were used instead of MRP. For BCRP, the primers used were (sense) 5'-TTA GGA TTG AAG CCA AAG G-3' (SEQ ID No. 5), and (antisense) 5'-TAG GCA ATT GTG AGG AAA ATA-3' (SEQ ID No. 6). The 5' end of the sense primer begins at nucleotide position 1727 of the BCRP cDNA (SEQ ID No. 2 and FIG. 2C); the 3' end of the antisense probe corresponds to position 2152 of the BCRP cDNA (FIG. 2C). The final concentrations of primers used was 200 nM. The final magnesium concentration used for PCR was 700 uM. Thirty-five cycles of denaturation (94° C., 1 minute), annealing (50° C., 1 minute) and elongation (72° C., 2 minutes) were carried out. Following agarose gel electrophoresis of an aliquot of the PCR reaction mixture, the gels were transferred to nitrocellulose and Southern blotting was done as described previously (12), using the 795 bp Clone 8 PCR product (5' end labeled with $^{32}$P-dCTP) as a probe for BCRP. The expected PCR product length is 446 bp.

Figure 7:
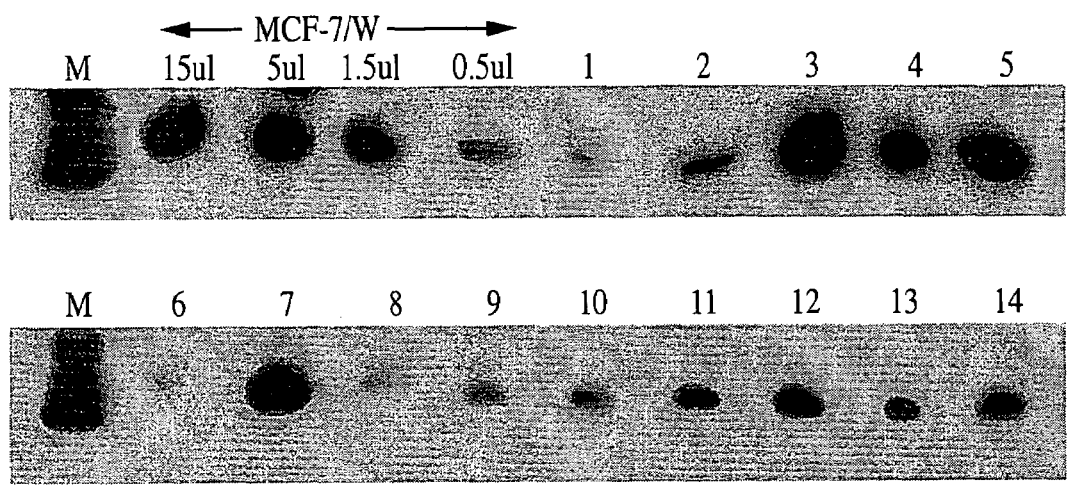
FIG. 7 is an autoradiograph showing the expression of BCRP in samples of blast cells from patients with acute myelogenous leukemia (AML). Detection of the expression of BCRP mRNA transcripts in MCF-7/W cells or in blast cells from 14 patients with AML is shown. Total cellular RNA was isolated as described previously (1), then 1 µg of RNA was added to a reverse-translation reaction mixture containing AMV reverse transcriptase, and oligonucleotide primers specific for beta-actin (10) or BCRP (see Example 11), as described previously (10). Following reverse-transcription, PCR was performed as described in Example 11, then an aliquot of the PCR reaction mix was subjected to agarose gel electrophoresis. For BCRP, the agarose gel was transferred to nitrocellulose membranes then Southern hybridization was done use $^{32}$P-labeled "clone-8 PCR product" as probe for BCRP. A radioautograph of this Southern blot is shown in this figure. M=DNA size marker. The number under MCF-7 indicates the µl of PCR reaction mixture that was added to the agarose gel lane. The numbers 1 to 14 indicate an AML patient blast cell sample; 15 µl of PCR reaction mix were added per gel lane for the AML samples. For beta actin, the PCR product on ethidium bromide stained gels was approximately equazl for the patient samples and for an equivalent amount of MCF-7/W PCR reaction mixture (data not shown).

Total cellular RNA was obtained from the blast cells of fourteen patients with AML. Controls were done using varying volumes of the PCR reaction mixture that was run with reverse-transcribed MCF-7/W RNA. The results of these controls and of the RT-PCR assays of the patient blast cell samples are depicted in FIG. 7. These controls using MCF-7/W RNA indicate the RT-PCR assay we developed is quantitative. Note in FIG. 7 that some patients have very low levels of expression of BCRP, while others (patients 3, 4, 5 and 7) have levels of expression comparable to or greater than that of MCF-7/W cells. This variation in expression of BCRP amongst blast cell samples from AML patients holds open the possibility that those patients who have relatively high expression of BCRP are more resistant to treatment with the anti-neoplastic drugs which are susceptible to the resistance caused by BCRP (anthracyclines and mitoxantrone). Mitoxantrone and the anthracycline daunorubicin are important drugs used in the treatment of AML.

Example 12

Northern Blot Hybridization in Various Cancer Cell Lines

Total cellular RNA was used for Northern analysis in all cases except for H209 or H69 cells, where poly $A^{30}$ RNA was used. RNA extraction and Northern blotting were performed by standard techniques, and as described in Example 4. A 795 bp fragment (clone 8, SEQ ID No. 7) of the 3' end of the 2418 bp BCRP cDNA was used as the hybridization probe after labeling with [$^{32}$P]-dCTP (PRIME-A-GENE™ labeling kit, Promega, Madison, Wis.). To control for variations in sample loading, the blots were stripped, then re-hybridized with $^{32}$P-labeled β-actin or 18S RNA probes.

Figure 8A:
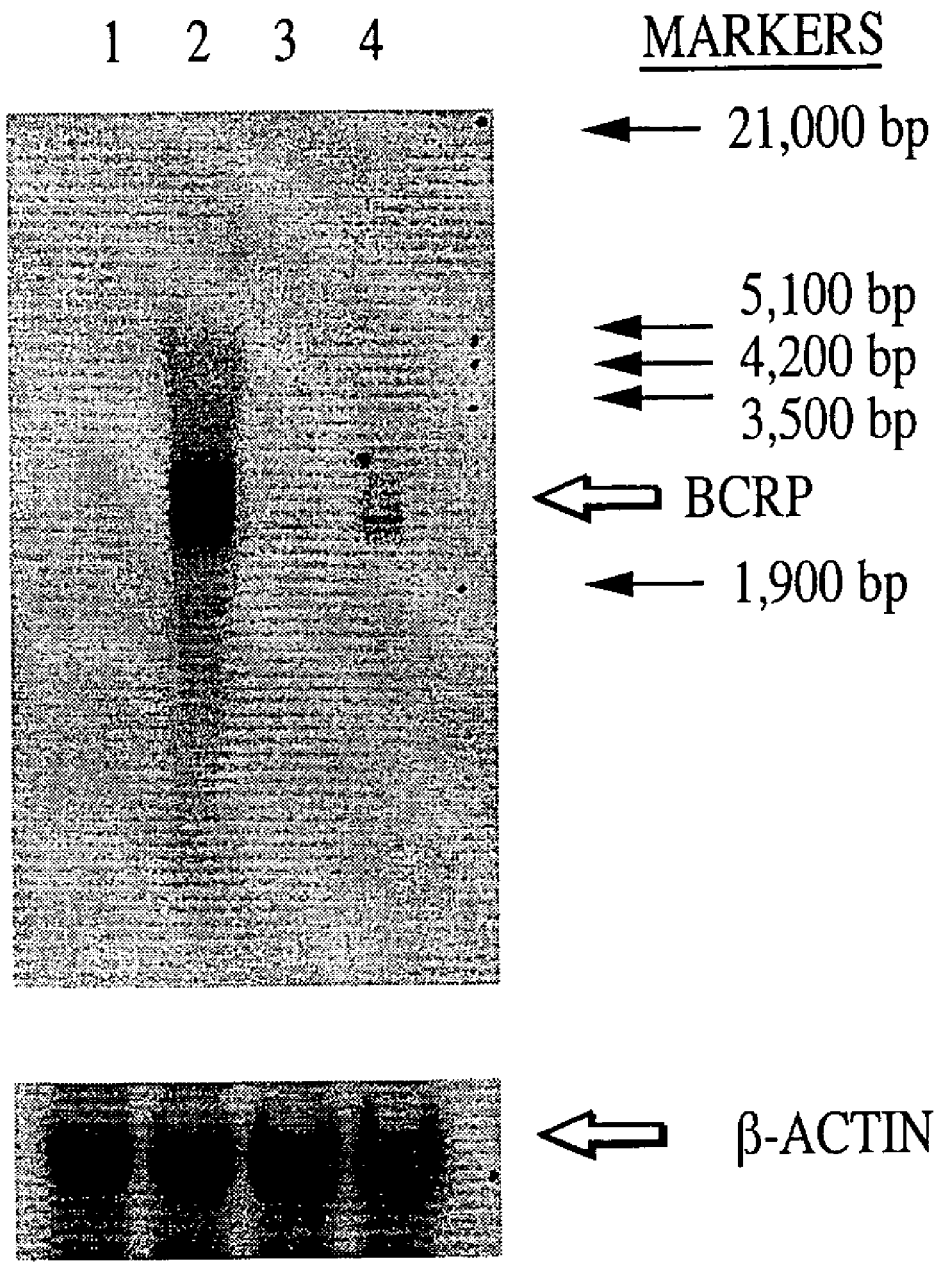
FIGS. 8A, 8B, and 8C are autoradiographs showing the results of Northern blot hybridizations of mRNA from various drug resistant cell lines probed with a BCRP probe.

FIG. 8A shows the results of the Northern blot hybridization of mRNA from MCF-7 cells (lane 1), MCF-7/MITOX (lane 2), 8226/W cells (lane 3), and 8226/MR20 (lane 4). The blot was probed for BCRP with a 795-bp cDNA (Cone 8, SEQ ID No. 7) after labeling with $^{32}$P-dCTP (top panel). To control for equivalence in sample loading, the blot was stripped and reprobed for β-actin (bottom panel).

Figure 8B:
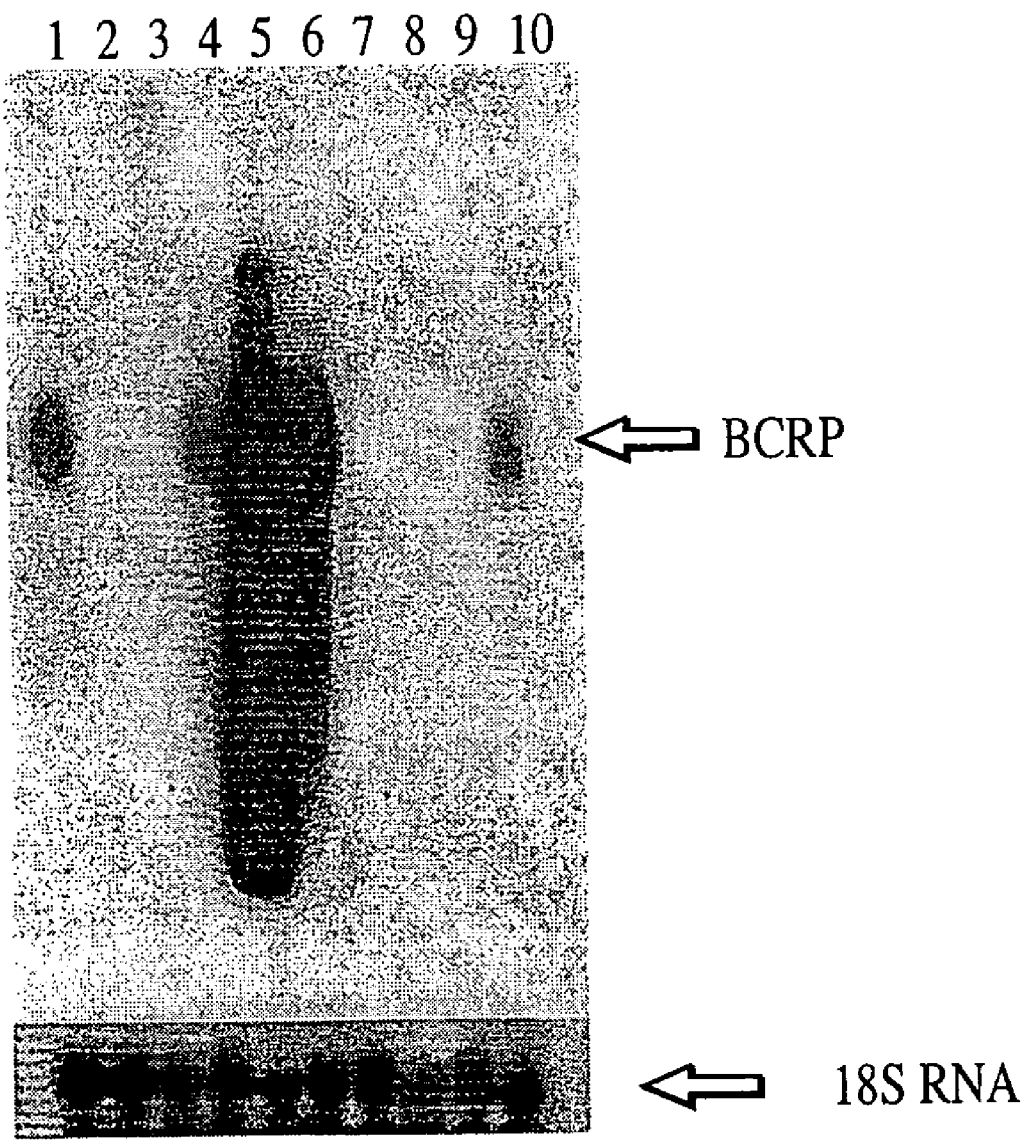

FIG. 8B shows the results of a Northern blot hybridization of mRNA from S1/M1-3.2 cells (lane 1), S1/W cells (lane 2), MCF-7/W cells (lane 3), MCF-7/MX$_{PR}$ cells (lane 4), MCF-7/MX$_{RS250}$ cells (lane 5), MCF-7/MX$_{RS600}$ cells (lane 6), MCF-7/VP (MRP+) cells (lane 7), MCF-7/Adr (Pgp+) cells (lane 8), MCF-7/MTX (DHFR+) cells (lane 9), MCF-7/AdrVp1000 (BCRP+) cells (lane 10). The blot was probed as described for FIG. 8A.

Figure 8C:
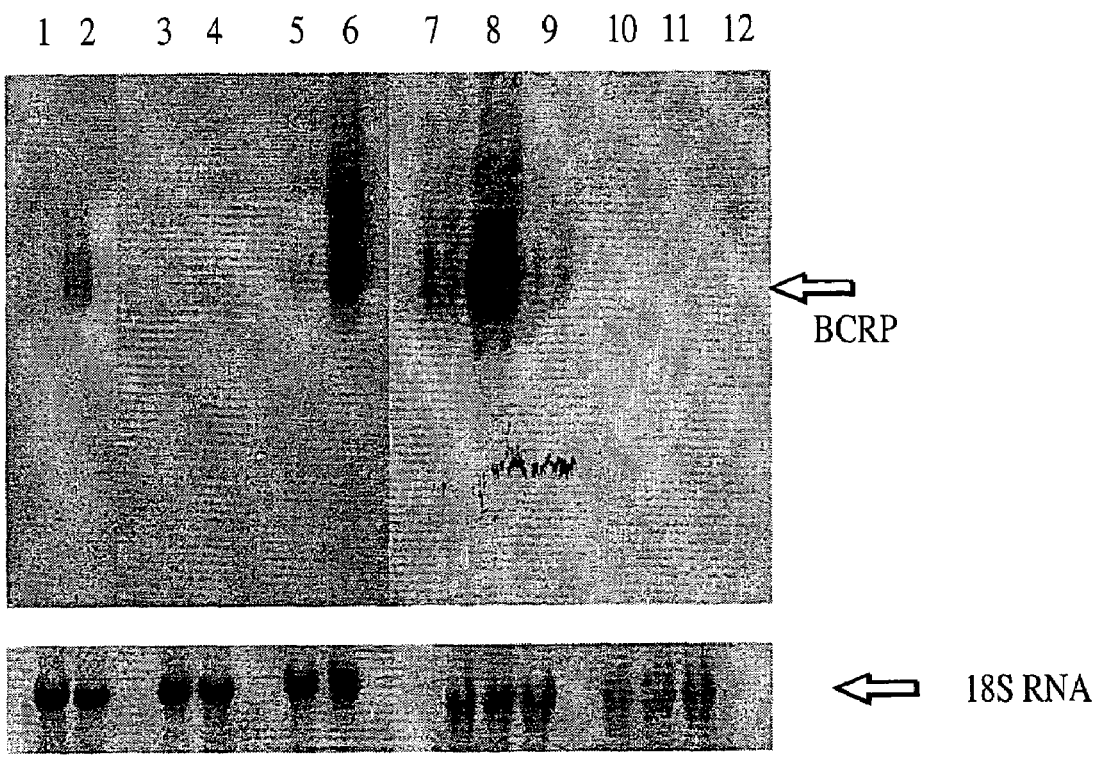

FIG. 8C shows a Northern blot hybridization of mRNA from human colon carcinoma HT29 cells (lane 1), HT29RNOV cells (lane 2), human breast carcinoma MDA-MB-231 cells (lane 3), MDA-MB-231RNOV cells (lane 4), human fibrosarcoma EPF86-079 cells (lane 5), EPF86-079RNOV cells (lane 6), human gastric carcinoma EPG85-257 cells (lane 7), EPG85-257RNOV cells (lane 8), EPG85-257RDB (Pgp+) cells (lane 9), human pancreatic carcinoma EPP85-181 cells (lane 10), EPP85-181RNOV cells (lane 11), and EPP85-181RDB (Pgp+) cells (lane 12). The blots were probed as described above for FIG. 8A.

Example 13

Southern Blot Hybridization

Figure 9:
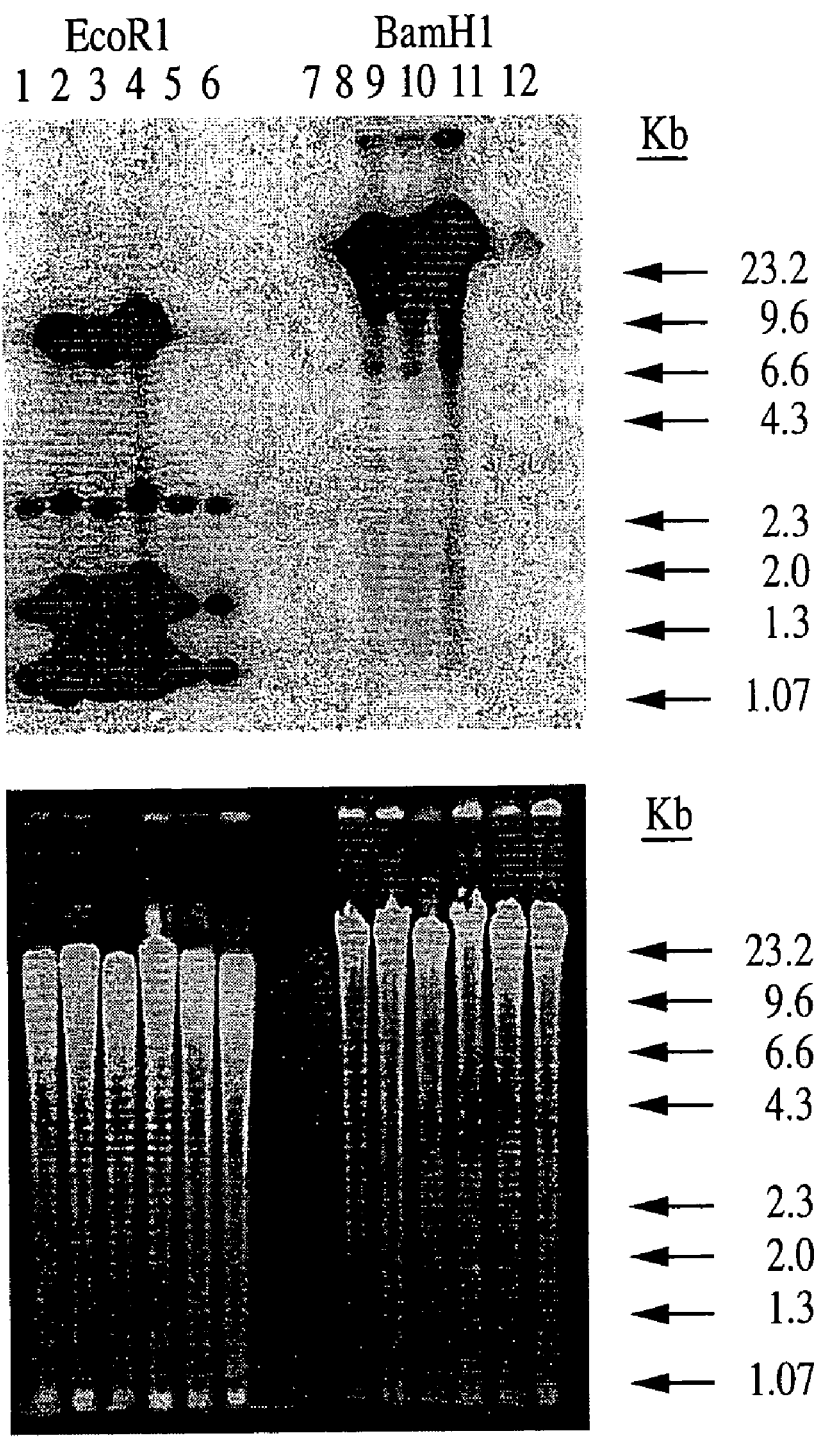
FIG. 9 is an autoradiograph of a Southern blot hybridization from various MCF-7 cell lines.

Genomic DNA was isolated using standard techniques (8) from the parental drug sensitive MCF-7/W cells (lanes 1, 7), MCF-7/MX$_{PR}$ cells (lanes 2, 8), MCF-7/MX$_{RS250}$ cells (lanes 3, 9), MCF-7/MX$_{RS600}$ cells (lanes 4, 10), MCF-7/VP cells (overexpress MRP, lanes 5, 11) and MCF-7/MTX cells (derive resistance by overexpression of DHFR, lanes 6, 12), digested with EcoR1 or BamH1, separated by 0.8% agarose gel electrophoresis, stained with ethidium bromide, transferred, and fixed to a nitrocellulose filter, using standard techniques (8). The filter was hybridized with the [$^{32}$P]-labeled 795 bp BCRP probe as described above for FIG. 8 (FIG. 9, top panel). Ethidium bromide stained 0.8% agarose gel electrophoresis of genomic DNA after digestion with the restriction endonucleases, and prior to nitrocellulose filter transfer, demonstrated approximate equivalency of sample loading (FIG. 9, bottom panel).

Example 14

Fumitremorgin C (FTC) Effects on BCRP Transfected Cells

MCF-7 cells transfected with either the pcDNA3 empty vector or pcDNA3 containing the full-length BCRP cDNA (transfectant clone 8) were cultured as monolayers in tissue culture flasks. The effects of FTC on the accumulation of the aza-anthrapyrazole BBR3390 were measured by exposing these cells to the fluorescent aza-anthrapyrazole BBR3390 (5 uM) in the presence or absence of 10 uM FTC for 60 minutes. Then, the cells were removed from the flasks by trypsinization, and intracellular BBR3390 content was measured by flow cytometry. The effects of FTC on BBR3390 retention were measured by exposing another set of cells (vector control and transfectant clone 8) to 5 uM BBR3390 with and without 10 uM FTC for 60 minutes, washing the cells free of drug, then reincubating the cells for an additional 30 minutes in fresh medium with and without FTC. Intracellular BBR3390 content was measured by flow cytometry. (See FIG. 10).

REFERENCES

1. Kessel D, Botterill V and Wodinsky I, Uptake and retention of daunomycin by mouse leukemia cells as factors in drug response, Cancer Res 28:938-941, 1968; Bewilder JCL and Rheum H, Cellular resistance to actinomycin D in Chinese Hamster cells in vitro: Cross-resistance, radioautographic, and cytogenetic studies. Cancer Res 30:1174-1184, 1970; Ling V and Thompson L H, Reduced permeability in CHO cells as a mechanism of resistance in a series of independently-derived VP-16 resistant human tumour cell lines, J Cell Physiol 83: 103-116, 1974.
2. Cole S P C, Bhardwaj G, Gerlach J H, Mackie J E, Grant C E, Almquist K C, Stewart A J, Kurz E U, Duncan A M V and Deeley R G: Overexpression of a transporter gene in a multidrug-resistant human lung cancer cell line. Science 258:1650-1654, 1992.
3. Chen Y-N, Mickley L A, Schwartz A M, Acton E M, Hwang J, Fojo A T. Characterization of adriamycin-resistant human breast cancer cells which display overexpression of a novel resistance-related membrane protein. J. Biol. Chem. 265:10073-10080, 1990.
4. Lee J S, Scala S, Matsumoto Y, Dickstein B, Robey R, Zhan Z, Altenberg G, Bates S E. Reduced drug accumulation and multidrug resistance in human breast cancer cells without associated P-glycoprotein or MRP overexpression. J Cell Biochem 65:513-526, 1997.
5. Doyle L A, Ross D D, Sridhara R, Fojo A T, Kaufmann S H, Lee E J, Schiffer C A. Expression of a 95 kDa membrane protein is associated with low daunorubicin accumulation in leukaemic blast cells. Br. J. Cancer 71, 52-58, 1995.
6. Liang P and Pardee A. Differential display of eukaryotic messenger RNA by means of the polymerase chain reaction. Science 257:967-971, 1992; Liang P, Averboukh L, Keyomarsi K, Sager R and Pardee A. Differential display and cloning of messenger RNAs from human breast cancer versus mammary epithelial cells. Cancer Res 52:6966-6968, 1992.
7. Kohler et al. (Nature 256:495 (1975); Eur. J. Immunol. 6:511 (1976); Euro J. Immunol. 6:292 (1976).
8. Maniatis, T. et al. In: Molecular Cloning, a Laboratory Manual, Cold Spring Harbor, N.Y. (1982), and by Haymes, B. D. et al., In: Nucleic Acid Hybridizations, A Practical Approach. IRL Press, Washington, D.C. (1985)
9. Morgan T H. Sex limited inheritance in Drosophila. Science 32:120-122, 1910; Bingham P M, Levis R, Rubin G M. Cloning of DNA sequences from the white locus of D melanogaster by a novel and general method. Cell 25:693-704, 1981; O'Hare K, Murphy C, Levis R, Rubin G M. DNA sequence of the white locus of Drosophila melanogaster. J Mol Biol 180:437-455, 1984; Pepling M, Mount S M. Sequence of a cDNA from the Drosophila melanogaster white gene. Nucleic Acids Res 18:1633, 1990; Chen H, Rossier C, Lalioti M D, Lynn A, Chakravarti A, Perrin G, Antonarkis S E. Cloning of the cDNA for a human homologue of the Drosophila white gene and mapping to Chromosome 21q22.3. Am J Hum Genet 59:66-75, 1996.
10. Ross D D, Doyle L A, Schiffer C A, Lee E J, Grant C E, Cole S P C, Deeley R G, Yang W and Tong Y. Expression of multidrug resistance-associated protein (MRP) mRNA in blast cells from acute myeloid leukemia (AML) patients. Leukemia 10:48-55, 1996.
11. Walker, J. E., Saraste, M., Runswick, M. J., Gay, N. J. Distantly related sequences in the alpha- and beta-subunits of ATP synthase, kinases, and other ATP-requiring enzymes and a common nucleotide binding fold. EMBO J. 1:945-951, 1982.
12. Pugh, E. L., Wakil, S. J. Studies on the mechanism of fatty acid synthesis. MV. The prosthetic group of acyl carrier protein and the mode of its attachment to protein. J. Biol. Chem. 240:4727-4733, 1965
13. Rao J K M, and Garos P. A conformational preference parameter to predict helices in integral membrane proteins. Biochim Biophys Acta 899:179-214, 1986.
14. Skehan P, Storeng R, Scudiero D, Monks A, McMahon J, Vistica D, Warren J T, Bokesch H, Kenny S, Boyd M R. New colorimetric cytotoxicity assay for anticancer drug screening. J Natl Cancer Inst 82:1107-1112, 1990.
15. Ross D D, Gao Y, Yang Y, Leszyk J, Shively J, Doyle L A. The 95-kilodalton membrane glycoprotein overexpressed in novel multidrug resistant breast cancer cells is NCA, the nonspecific cross-reacting antigen of carcinoembryonic antigen. Cancer Res 57:5460-5464, 1997.
16. Kawaharata H, Hinoda Y, Itoh F, Endo T, Oikawa S, Nakazato H, Imai K. Decreased sensitivity of carcinoembryonal antigen cDNA-transfected cells to adriamycin. Int J Cancer 72, 377-382, 1997. 1. Ausubel F M, Brent R, Kingston R E, Moore D D, Seidman J G, Smith J A, and Struhl K, editors. Current protocols in molecular biology, volume 1, chapter 9. John Wiley and Sons, N.Y., 1989.
17. Harker W G, Slade D L, Dalton W S, Meltzer P S, Trent J M. Multidrug resistance in mitoxantrone-selected HL-60 leukemia cells in the absence of P-glycoprotein overexpression. Cancer Res 49:4542-4549, 1989.
18. Taylor C W, Dalton W S, Parrish P R, Gleason M C, Bellamy W T, Thompson F H, Roe D J, Trent J M. Different mechanisms of deceased drug accumulation in doxorubicin and mitoxantrone resistant variants of the MCF-7 human breast cancer cell line. Br J Cancer 63:923-929, 1991.
19. Nakagawa M, Schneider E, Dixon K H,m Horton J, Kelley K, Morrow C, Cowan K. Reduced intracellular drug accumulation in the absence of P-glycoprotein (mdr1) overexpression in mitoxantrone-resistant human MCF-7 breast cancer cells. Cancer Res 52:6175-6181, 1992.
20. Yang C-H J, Cowan K, Schneider E. Reselection of a mitoxantrone-resistant breast carcinoma cell line with mitoxantrone results in a parallel increase in cross-resistance to camptothecin analogues. Proc Amer Assoc Cancer Res (abstract) 37:308, 1996.
21. Schneider E, Horton J K, Yang C-H, Nakagawa M, Cowan K H. Multidrug resistance-associated protein gene overexpression and reduced drug sensitivity of topoisomerase II in a human breast carcinoma MCF7 cell line selected for etoposide resistance. Cancer Res 54:152-158, 1994.
22. Fairchild C R, Ivy P S, Kao-Shan C-S, Whang-Peng J, Rosen N, Israel M A, Melera P W, Cowan K H, Goldsmith M E. Isolation of amplified and overexpressed DNA seqeunces from adreamycin-resistant human breast cancer cells. Cancer Res 47:5141-5148, 1987.
23. Cowan K H, Goldsmith M E, Levine R M, Aitken S C, Douglass E, Clendeninn N, Neinhuis A W, Lipman M E. Dihydrofolate reductase gene amplification and possible rearrangement in estrogen-responsive methotrexate resistant human breast cancer cells. J Biol Chem 257:15079-15086, 1982.
24. Futcher B W, Abbaszadegan M R, Domann F, Dalton W S. Analysis of MRP mRNA in mitoxantrone-selected, multidrug resistant human tumor cells. Biochem Pharm 47:1601, 1994.
25. Rabindran S K, He H, Singh M, Brown E, Collins K I, Annable T, Greenberger L M. Reversal of a novel multidrug resistance mechanism in human colon carcinoma cells by fumitremorgin C. Cancer Res 58:5850-5858, 1998.
26. Yu Q, Mirski S E L, Sparks K E, Cole S P C. Two COOH-truncated cytoplasmic forms of topoisomerase IIα in a VP-16 selected lung cancer cell line result from partial gene deletion and alternative splicing. Biochemistry 36:5868-5877, 1997.
27. Dietel M, Arps H, Lage H, Neindorf A. Membrane vesicle formation due to acquired mitoxantrone resistance in human gastric carcinoma cell line EPG85-257. Cancer Res 50:6100-6106, 1990.
28. Kellner U, Hutchinson L, Seidel A, Lage H, Danks M K, Deitel M, Kaufmann S H. Decreased drug accumulation in a mitoxantrone-resistant gastric carcinoma in the absence of P-glycoprotein. Int J Cancer 71:817-824, 1997.
29. Holm P S, Scanlon K J, Dietel M. Reversion of multidrug resistance in the P-glycoprotein-positive human pancreatic cell lin (EPP85-181RDB) by introduction of a hammerhead ribozyme. Br J Cancer 70:239-243, 1994.
30. Harker W G, Slade D L, Dalton W S, Meltzer P S, Trent J M. Multidrug resistance in mitoxantrone-selected HL-60 leukemia cells in the absence of P-glycoprotein overexpression. Cancer Res 49:4542-4549, 1989.

TABLE 1

Characteristics of Selected Multidrug Resistant Human Cancer Cell Lines

| Cell line | Tumor origin | Fold resistance to selecting agent | Selecting agent | Expression levels relative to parental cell line | | | References |
|---|---|---|---|---|---|---|---|
| | | | | Pgp | MRP | BCRP | |
| MCF-7/Mitox | breast | 1,208 | mitoxantrone | − | − | ++ | 18 |
| MCF-7/MX$_{PR}$ | " | 270 | " | − | +/− | ++ | 19 |
| MCF-7/MX$_{RS250}$ | " | 4,600 | " | − | +/− | +++ | 20 |
| MCF-7/MX$_{RS600}$ | " | 7,450 | " | − | − | +++ | 20 |
| MCF-7/AdrVp1000 | " | 4,000 | dox verap | − | − | + | 3, 4 |
| MCF-7/AdrVp3000 | " | −7,000 | " | − | − | ++ | 3, 4 |
| MCF-7/Vp | " | 26 | etoposide | − | ++ | − | 21 |
| MCF-7/Adr | " | 192 | daunorubicin | ++ | − | − | 22 |
| MCF-7/MTX | " | 1,000 | methotrecate | − | − | − | 23 |
| MDA-MB-231RNOV | " | 93 | mitoxantrone | − | − | +/− | H. Lage, unpublished |
| 5226/MR20 | myeloma | 36 | mitoxantrone | − | − | + | 24 |
| S1M1-3.2 | colon | 1,435 | mitoxantrone | − | − | + | 25 |
| HT29RNOV | " | 100 | mitoxantrone | +/− | − | + | H. Lage, unpublished |
| H209/MX2 | small cell lung | 2 | mitoxantrone | − | − | − | S. Cola, unpublished |
| H209/MX4 | " | 4 | " | − | − | − | " |
| H209/V6 | " | 22 | etoposide | − | − | − | 26 |
| H69/AR | " | 100 | daunorubicin | − | +++ | − | 2 |
| EPF86-257RNOV | gastric | 457 | mitoxantrone | − | − | ++ | 27, 28 |
| EPF86-257RDB | " | 1,857 | daunorubicin | ++ | − | − | 27, 28 |
| EPP85-181RNOV | pancreatic | 27 | mitoxantrone | − | − | − | H. Lage, unpublished |
| EPP85-181RDB | " | 848 | daunorubicin | ++ | − | − | 29 |
| EPF86-079RNOV | fibrosarcoma | 7 | mitoxantrone | − | − | ++ | H. Lage, unpublished |
| HL-60/MX2 | leukemia | 35 | mitoxantrone | − | − | − | 30 |

We claim:

1. A purified polypeptide comprising the amino acid sequence set forth in SEQ ID NO:1.

2. A purified polypeptide consisting of the amino acid sequence set forth in SEQ ID NO:1.

3. An isolated cell comprising a vector comprising a polynucleotide fully encoding a polypeptide comprising the amino acid sequence set forth in SEQ ID NO:1.

4. An isolated cell comprising a vector comprising a polynucleotide fully encoding a polypeptide consisting of the amino acid sequence set forth in SEQ ID NO:1.

* * * * *